(12) United States Patent  
Fritzinger et al.

(10) Patent No.: US 8,728,129 B2
(45) Date of Patent: May 20, 2014

(54) VARIABLE ANGLED LOCKING SCREW

(75) Inventors: Daniel Duane Fritzinger, Warsaw, IN (US); Bryce Alan Isch, Bluffton, IN (US); William J. Hamman, Winona Lake, IN (US); Benjamin Paul Heilman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 552 days.

(21) Appl. No.: 12/986,879

(22) Filed: Jan. 7, 2011

(65) Prior Publication Data

US 2012/0177462 A1 Jul. 12, 2012

(51) Int. Cl.
*A61B 17/80* (2006.01)
*A61B 17/88* (2006.01)

(52) U.S. Cl.
USPC ............ 606/290; 606/71; 606/288; 606/293; 606/294; 606/104; 606/915; 606/916

(58) Field of Classification Search
USPC .................. 606/267–269, 271, 272, 65, 66, 606/280–299, 303, 305–308, 319, 328; 411/26, 397, 537
See application file for complete search history.

(56) References Cited

U.S. PATENT DOCUMENTS

| | | |
|---|---|---|
| 987,033 A | 3/1911 | Allison |
| 2,230,534 A | 2/1941 | Elmer et al. |
| 3,069,924 A | 12/1962 | Watanabe et al. |
| 3,289,522 A | 12/1966 | Bell |
| 3,426,819 A | 2/1969 | Estes et al. |
| 4,006,660 A | 2/1977 | Yamamoto et al. |
| 5,234,431 A | 8/1993 | Keller |
| 5,269,784 A | 12/1993 | Mast |
| 5,326,206 A | 7/1994 | Moore |
| 5,364,399 A | 11/1994 | Lowery et al. |
| 5,456,719 A | 10/1995 | Keller |
| 5,476,880 A | 12/1995 | Cooke et al. |

(Continued)

FOREIGN PATENT DOCUMENTS

WO WO 2005/018698 A1 3/2005
WO WO 2008145902 A2 * 12/2008 ............ A61B 17/80

(Continued)

OTHER PUBLICATIONS

Unknown, VariAx Foot Locking Plate System, c 2007 Stryker, pp. 1-15, Stryker Leibinger BmbH & Co. KG, Germany.

(Continued)

*Primary Examiner* — Michael T Schaper
(74) *Attorney, Agent, or Firm* — Ryan O. White; Taft, Stettinius & Hollister

(57) ABSTRACT

A variable angle locking screw assembly that includes a plate material, a screw, and a washer at least partially located within the plate material, the washer and screw cooperating to create a wedge locking the screw in one of a plurality of axial and rotational positions, where the locked position may be undone and adjusted by manipulation of at least one of the screw and washer.

7 Claims, 24 Drawing Sheets

(56) References Cited

U.S. PATENT DOCUMENTS

| | | | |
|---|---|---|---|
| 5,482,463 | A | 1/1996 | Wilson, Jr. et al. |
| 5,501,684 | A | 3/1996 | Schlapfer et al. |
| 5,534,027 | A | 7/1996 | Hodorek |
| 5,534,032 | A | 7/1996 | Hodorek |
| 5,575,792 | A | 11/1996 | Errico et al. |
| 5,578,034 | A | 11/1996 | Estes |
| 5,591,234 | A | 1/1997 | Kirsch |
| 5,607,428 | A | 3/1997 | Lin |
| 5,609,594 | A | 3/1997 | Errico et al. |
| 5,690,631 | A | 11/1997 | Duncan et al. |
| 5,702,457 | A | 12/1997 | Walch et al. |
| 5,776,194 | A | 7/1998 | Mikol et al. |
| 5,876,402 | A | 3/1999 | Errico et al. |
| 5,931,838 | A | 8/1999 | Vito |
| 5,954,722 | A | 9/1999 | Bono |
| 5,984,924 | A | 11/1999 | Asher et al. |
| 6,004,323 | A | 12/1999 | Park et al. |
| 6,030,389 | A | 2/2000 | Wagner et al. |
| 6,187,005 | B1 | 2/2001 | Brace et al. |
| 6,193,720 | B1 | 2/2001 | Yuan et al. |
| 6,206,881 | B1 | 3/2001 | Frigg et al. |
| 6,261,291 | B1 | 7/2001 | Talaber et al. |
| 6,309,397 | B1 | 10/2001 | Julian et al. |
| 6,315,779 | B1 | 11/2001 | Morrison et al. |
| 6,322,562 | B1 | 11/2001 | Wolter |
| 6,331,179 | B1 | 12/2001 | Freid et al. |
| 6,454,769 | B2 | 9/2002 | Wagner et al. |
| 6,471,706 | B1 | 10/2002 | Schumacher et al. |
| 6,533,786 | B1 | 3/2003 | Needham et al. |
| 6,599,290 | B2 | 7/2003 | Bailey et al. |
| 6,663,632 | B1 | 12/2003 | Frigg |
| 6,663,635 | B2 | 12/2003 | Frigg et al. |
| 6,679,883 | B2 | 1/2004 | Hawkes et al. |
| 6,692,498 | B1 | 2/2004 | Niiranen et al. |
| 6,692,503 | B2 | 2/2004 | Foley et al. |
| 6,695,846 | B2 | 2/2004 | Richelsoph et al. |
| 6,702,817 | B2 | 3/2004 | Beger et al. |
| 6,730,091 | B1 | 5/2004 | Pfefferle et al. |
| 6,736,820 | B2 | 5/2004 | Biedermann et al. |
| 6,746,453 | B2 | 6/2004 | Deloge et al. |
| 6,780,186 | B2 | 8/2004 | Errico et al. |
| 6,808,527 | B2 | 10/2004 | Lower et al. |
| 6,840,938 | B1 | 1/2005 | Morley et al. |
| 6,893,443 | B2 | 5/2005 | Frigg et al. |
| 6,955,677 | B2 | 10/2005 | Dahners |
| 6,964,664 | B2 | 11/2005 | Freid et al. |
| 7,001,387 | B2 | 2/2006 | Farris et al. |
| 7,001,389 | B1 | 2/2006 | Navarro et al. |
| 7,008,426 | B2 | 3/2006 | Paul |
| 7,048,739 | B2 | 5/2006 | Konieczynski et al. |
| 7,063,701 | B2 | 6/2006 | Michelson |
| 7,063,702 | B2 | 6/2006 | Michelson |
| 7,077,844 | B2 | 7/2006 | Michelson |
| 7,090,676 | B2 | 8/2006 | Huebner et al. |
| 7,097,645 | B2 | 8/2006 | Michelson |
| 7,112,202 | B2 | 9/2006 | Michelson |
| 7,125,403 | B2 | 10/2006 | Julian et al. |
| 7,153,329 | B2 | 12/2006 | Wilson |
| 7,169,150 | B2 | 1/2007 | Shipp et al. |
| 7,175,624 | B2 | 2/2007 | Konieczynski et al. |
| 7,195,633 | B2 | 3/2007 | Medoff et al. |
| 7,207,992 | B2 | 4/2007 | Ritland |
| 7,229,442 | B2 | 6/2007 | Schafer |
| 7,273,481 | B2* | 9/2007 | Lombardo et al. ......... 606/86 A |
| 7,306,597 | B2 | 12/2007 | Manzo |
| 7,309,340 | B2 | 12/2007 | Fallin et al. |
| 7,314,487 | B2 | 1/2008 | Ralph et al. |
| 7,322,983 | B2 | 1/2008 | Harris |
| 7,335,205 | B2 | 2/2008 | Aeschlimann et al. |
| 7,367,973 | B2 | 5/2008 | Manzo et al. |
| 7,399,150 | B2 | 7/2008 | Hofschneider |
| 7,410,496 | B2 | 8/2008 | Derouet |
| 7,524,325 | B2 | 4/2009 | Khalili |
| 7,547,306 | B2 | 6/2009 | Michelson |
| 7,637,928 | B2 | 12/2009 | Fernandez |
| 7,641,676 | B2 | 1/2010 | Mathieu et al. |
| 7,651,497 | B2 | 1/2010 | Michelson |
| 7,662,155 | B2 | 2/2010 | Metzger et al. |
| 7,678,113 | B2 | 3/2010 | Melkent |
| 7,846,163 | B2* | 12/2010 | Fourcault et al. ............... 606/68 |
| 8,114,140 | B2* | 2/2012 | Derouet ..................... 606/305 |
| 8,617,223 | B2* | 12/2013 | Matityahu ................... 606/290 |
| 2002/0029040 | A1 | 3/2002 | Morrison et al. |
| 2002/0058939 | A1 | 5/2002 | Wagner et al. |
| 2003/0078583 | A1 | 4/2003 | Biedermann et al. |
| 2004/0199258 | A1 | 10/2004 | Macara |
| 2004/0236330 | A1 | 11/2004 | Purcell et al. |
| 2004/0267261 | A1* | 12/2004 | Derouet ..................... 606/70 |
| 2005/0015131 | A1* | 1/2005 | Fourcault et al. ............. 607/116 |
| 2005/0096502 | A1 | 5/2005 | Khalili |
| 2005/0143742 | A1 | 6/2005 | Porcher |
| 2005/0192571 | A1 | 9/2005 | Abdelgany |
| 2005/0192572 | A1 | 9/2005 | Abdelgany et al. |
| 2005/0216008 | A1 | 9/2005 | Zwirnmann et al. |
| 2005/0251137 | A1 | 11/2005 | Ball |
| 2005/0251141 | A1 | 11/2005 | Frigg et al. |
| 2005/0273165 | A1 | 12/2005 | Griffiths et al. |
| 2006/0016300 | A1 | 1/2006 | Bubel |
| 2006/0058797 | A1 | 3/2006 | Mathieu et al. |
| 2006/0079884 | A1 | 4/2006 | Manzo et al. |
| 2006/0079889 | A1 | 4/2006 | Scott |
| 2006/0100626 | A1 | 5/2006 | Rathbun et al. |
| 2006/0116678 | A1 | 6/2006 | Impellizzeri |
| 2006/0122604 | A1 | 6/2006 | Gorhan et al. |
| 2006/0224044 | A1 | 10/2006 | Marchek et al. |
| 2006/0235400 | A1 | 10/2006 | Schneider |
| 2006/0241618 | A1* | 10/2006 | Gasser et al. ................... 606/72 |
| 2007/0038214 | A1 | 2/2007 | Morley et al. |
| 2007/0055251 | A1 | 3/2007 | Huebner et al. |
| 2007/0088360 | A1 | 4/2007 | Orbay et al. |
| 2007/0093827 | A1 | 4/2007 | Warnick |
| 2007/0162016 | A1 | 7/2007 | Matityahu |
| 2007/0162019 | A1 | 7/2007 | Burns et al. |
| 2007/0212915 | A1 | 9/2007 | Strnad et al. |
| 2007/0270851 | A1 | 11/2007 | Erickson et al. |
| 2008/0033437 | A1 | 2/2008 | Shipp et al. |
| 2008/0046122 | A1 | 2/2008 | Manzo et al. |
| 2008/0114359 | A1 | 5/2008 | Murner et al. |
| 2008/0119870 | A1 | 5/2008 | Williams |
| 2008/0119895 | A1 | 5/2008 | Manceau |
| 2008/0172130 | A1 | 7/2008 | Macara |
| 2008/0177291 | A1 | 7/2008 | Jensen et al. |
| 2008/0234677 | A1 | 9/2008 | Dahners et al. |
| 2008/0234749 | A1 | 9/2008 | Forstein |
| 2008/0243141 | A1 | 10/2008 | Privitera et al. |
| 2008/0243192 | A1 | 10/2008 | Jacene et al. |
| 2008/0281272 | A1 | 11/2008 | Blundred et al. |
| 2008/0288000 | A1 | 11/2008 | Cawley |
| 2008/0300637 | A1 | 12/2008 | Austin et al. |
| 2009/0088807 | A1 | 4/2009 | Castaneda et al. |
| 2009/0131938 | A1 | 5/2009 | Khatri et al. |
| 2009/0143824 | A1 | 6/2009 | Austin et al. |
| 2009/0182337 | A1 | 7/2009 | Stopek et al. |
| 2009/0192550 | A1 | 7/2009 | Leung et al. |
| 2009/0232618 | A1 | 9/2009 | Ballenger |
| 2009/0248087 | A1 | 10/2009 | Lewis et al. |
| 2009/0299369 | A1 | 12/2009 | Orbay et al. |
| 2010/0011900 | A1 | 1/2010 | Burbank |
| 2010/0011901 | A1 | 1/2010 | Burbank |
| 2010/0016858 | A1 | 1/2010 | Michel |
| 2010/0057127 | A1 | 3/2010 | McGuire et al. |
| 2010/0069969 | A1* | 3/2010 | Ampuero et al. ............. 606/301 |
| 2010/0174324 | A1* | 7/2010 | Derouet ..................... 606/305 |
| 2011/0015682 | A1* | 1/2011 | Lewis et al. ................. 606/305 |
| 2011/0152945 | A1* | 6/2011 | Matityahu ................... 606/290 |
| 2011/0172666 | A1 | 7/2011 | Heilman |
| 2011/0270320 | A1* | 11/2011 | Oh et al. .................... 606/290 |
| 2012/0010666 | A1* | 1/2012 | Songer ...................... 606/286 |
| 2012/0143193 | A1* | 6/2012 | Hulliger ..................... 606/70 |

(56) References Cited

U.S. PATENT DOCUMENTS

| | | | |
|---|---|---|---|
| 2013/0018426 A1* | 1/2013 | Tsai et al. | 606/290 |
| 2013/0304132 A1* | 11/2013 | Heilman | 606/281 |
| 2013/0317554 A1* | 11/2013 | Purcell | 606/319 |

FOREIGN PATENT DOCUMENTS

| | | |
|---|---|---|
| WO | WO 2010/030845 A1 | 3/2010 |
| WO | PCT/US2011/020607 | 5/2011 |
| WO | WO 2011/085272 A1 | 7/2011 |
| WO | PCT/US2011/020607 | 7/2012 |

OTHER PUBLICATIONS

Unknown, Cannulated Screws 3.0/3.5/4.0/4.5/6.5/7.0/7.3, c 2004 Stratec Medical, pp. 1-18, Synthes, Oberdorf, Switzerland.

Unknown, Surgical Technique: Lumbar I/F Cage System, c 2002 DePuy AcroMed, pp. 1-22, DePuy AcroMed, Inc., Raynham, Mass.

Larson et al., Locking Plate Technology and its Applications in Upper Extremity Fracture Care, Hand Clinics 23 (2007) 269-278, c 2007, Elsevier Inc., USA.

Jacobs, The Effect of Innovative Screw Angled Mini-Plates on Biomechanical Stability of Mono-Cortical Fixation, Univ. of Pretoria, Chs. 1 & 2, (2009) pp. 7-29.

* cited by examiner

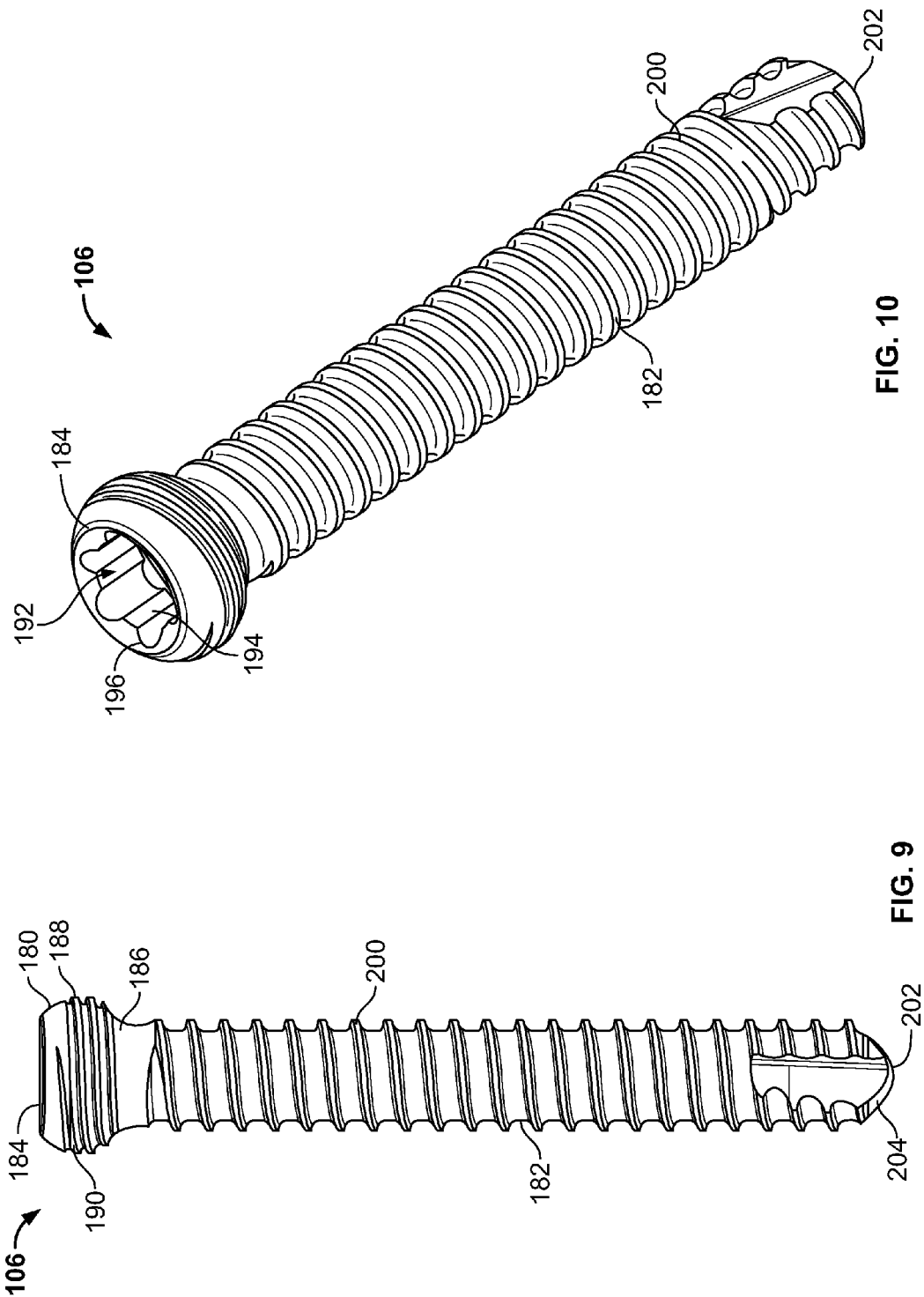

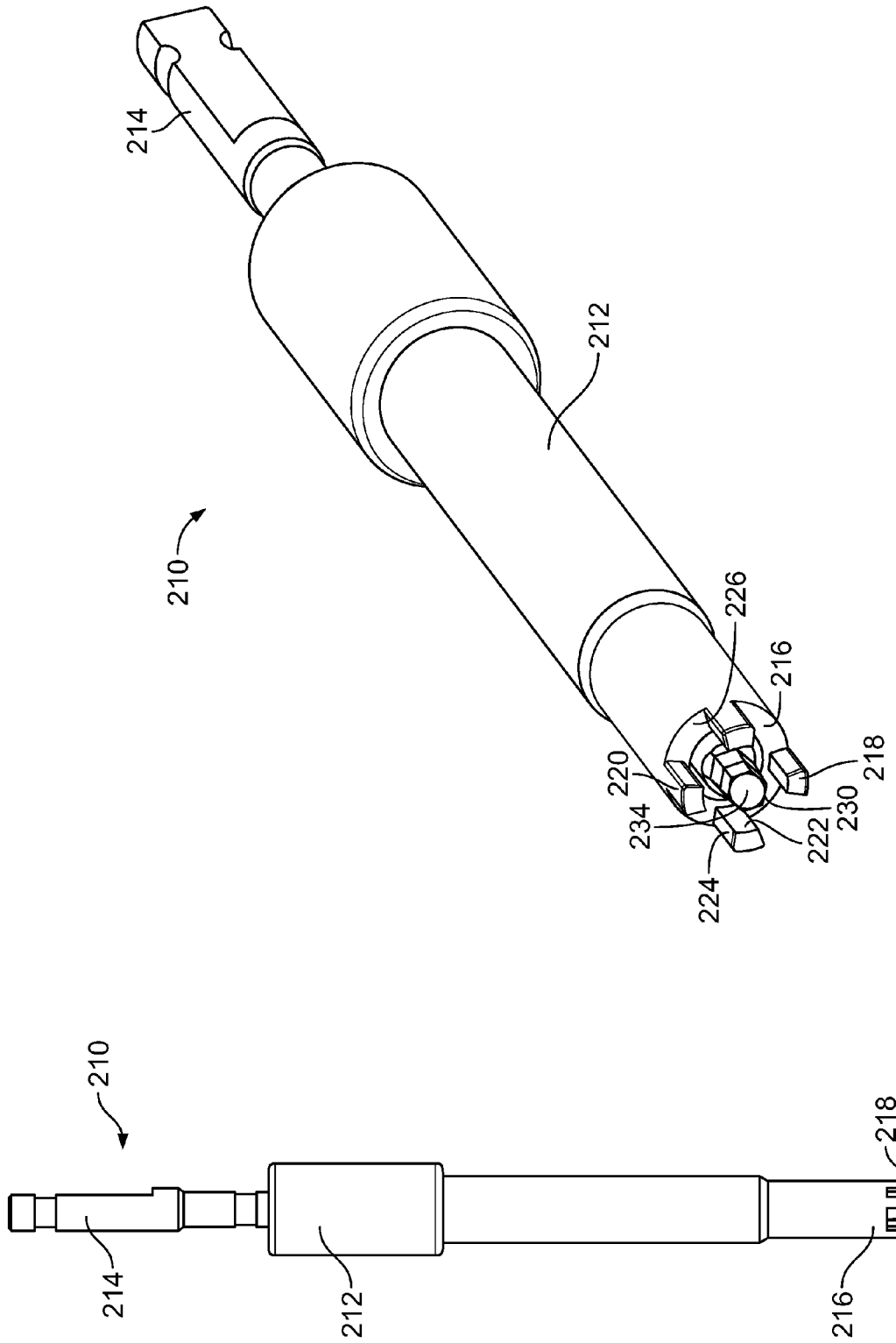

VARIABLE ANGLED LOCKING SCREW

FIELD OF THE INVENTION

The present disclosure relates to fasteners and more specifically, encompasses fasteners for use in surgical applications where the fastener may be oriented in any one of a plurality of angles with respect to a substrate material and subsequently secured in one of a plurality of possible angular rotational and axial orientations.

INTRODUCTION TO THE INVENTION

It is a first aspect of the present invention to provide a locking screw assembly comprising: (a) a plate material basing a through hole at least partially defined by a semispherical wall; (b) a first washer at least partially defining a first opening and being insertable into the through hole, the first washer includes a widthwise dimension substantially greater than a thickness; (c) a second washer at least partially defining a second opening and being insertable into the through hole, the second washer includes a widthwise dimension substantially greater than a thickness; (d) a screw including a threaded head and a longitudinal threaded shall extending from the threaded head, the screw is insertable into the through hole, where the first opening and second opening are sized to allow throughput of the longitudinal threaded shaft, and where the semispherical wall is sized to retain the first washer and the second washer within the through hole.

In a more detailed embodiment of the first aspect, the invention further includes a driver including a first engagement device and a second engagement device, wherein the first engagement device is rotatably repositionable with respect to the second engagement device. In yet another more detailed embodiment, the second opening of the second washer is sized to inhibit throughput of the threaded head of the screw, and the first opening of the first washer is sized to at least partially receive the threaded head of the screw. In a further detailed embodiment, at least one of the first washer and the second washer is discontinuous. In still a further detailed embodiment, the through hole of the plate material includes a widthwise dimension greater than a vertical dimension. In a more detailed embodiment, the through hole of the plate material includes at least two cutouts extending into the semispherical wall, the at least two cutouts being oriented horizontally across from one another. In a more detailed embodiment, the at least two cutouts are both oriented on the same side of a horizontal diametric chord of the through hole. In another more detailed embodiment, at least one of the first washer and the second washer includes a rounded circumferential surface interposing a top surface and a bottom surface. In yet another more detailed embodiment, the rounded circumferential surface is at least one of smooth and textured. In still another more detailed embodiment, at least one of the first washer and the second washer includes a sloped circumferential surface interposing a top surface and a bottom surface.

In yet another more detailed embodiment of the first aspect, the sloped circumferential surface is at least one of smooth and textured. In still another more detailed embodiment a wall at least partially defining the first opening of the first washer is threaded. In a further detailed embodiment, a wall defining the second opening of the second washer is not threaded. In still a further detailed embodiment, the first opening of the first washer is partially defined by at least threaded wall segments, each of the threaded wall segments being circumferentially spaced from one another and interposed by a circumferential discontinuity. In a more detailed embodiment, the first opening of the first washer is partially defined by four threaded wall segments, each of the threaded wall segments being circumferentially spaced from one another by a separate circumferential discontinuity. In a more detailed embodiment, each circumferential discontinuity is defined by an axially inset wall of the first washer having a U-shaped cross-section, wherein the discontinuity is adapted to receive a driver. In another more detailed embodiment, the longitudinal threaded shaft of the screw includes threads having a first pitch and a first thread depth, the threaded head of the screw includes threads having a second pitch and a second thread depth, the first pitch is greater than the second pitch, and the first thread depth is greater than the second thread depth. In yet another more detailed embodiment the base of the threaded head of the screw is tapered and the tapered surface is generally smooth.

In a more detailed embodiment of the first aspect, the second opening of the second washer is at least partially defined by a rounded over surface extending between a horizontal top surface and a wall predominantly defining the second opening. In yet another more detailed embodiment, the threaded head of the screw includes a spherical exterior surface. In a further detailed embodiment, the invention further includes a third washer defining a third opening and being insertable into the through hole, the third washer includes a widthwise dimension substantially greater than a thickness. In still a further detailed embodiment, the third washer is a spring washer. In a more detailed embodiment, the third washer comprises at least one of a helical washer, a Belleville washer, a wave spring washer, and a helical coil. In a more detailed embodiment, the through hole of the plate material includes at least two cutouts extending vertically into the semispherical wall, but not completely through the plate material, the at least two cutouts being oriented horizontally across from one another, in another more detailed embodiment, the at least two cutouts include a widthwise dimension greater than the cumulative total thickness of the first washer, the second washer, and the third washer.

It is a second aspect of the present invention to provide a locking screw assembly comprising: (a) a plate material having a through hole at least partially defined by a first semispherical wall segment and a second semispherical wall segment; (b) a first washer at least partially defining a first opening and being insertable into the through hole, the first washer includes a widthwise dimension substantially greater than a thickness; (c) a second washer at least partially defining a second opening and being insertable into the through hole, the second washer includes a widthwise dimension substantially greater than a thickness; (d) a screw including a threaded head and a longitudinal threaded shaft extending from the threaded head, the screw is insertable into the through hole, where the first opening and second opening are sized to allow throughput of the longitudinal threaded shaft, and where the first semispherical wall segment and second hemispherical wall segment are sized to retain the first washer and the second washer within the through hole.

In a more detailed embodiment of the second aspect, the invention further includes a driver including a first engagement device and a second engagement device, wherein the first engagement device is rotatably repositionable with respect to the second engagement device. In yet another more detailed embodiment, the second opening of the second washer is sized to inhibit throughput of the threaded head of the screw, and the first opening of the first washer is sized to at least partially receive the threaded head of the screw. In a further detailed embodiment, at least one of the first washer and the second washer is discontinuous. In still a further detailed embodiment, the through hole of the plate material includes a widthwise dimension greater than a vertical dimension. In a more detailed embodiment, the through hole of the plate material includes at least two cutouts extending into the semispherical wall, the at least two cutouts being oriented horizontally across from one another. In a more detailed embodiment, the at least two cutouts are both oriented on the same side of a horizontal diametric chord of the through hole. In another more detailed embodiment, at least one of the first washer and the second washer includes a rounded circumferential surface interposing a top surface and a bottom surface. In yet another more detailed embodiment, the rounded circumferential surface is at least one of smooth and textured. In still another more detailed embodiment, at least one of the first washer and the second washer includes a sloped circumferential surface interposing a top surface and a bottom surface.

In yet another more detailed embodiment of the second aspect, the sloped circumferential surface is at least one of smooth and textured. In still another more detailed embodiment, a wall at least partially defining the first opening of the first washer is threaded. In a further detailed embodiment, a wall defining the second opening of the second washer is not threaded. In still a further detailed embodiment, the first opening of the first washer is partially defined by at least threaded wall segments, each of the threaded wall segments being circumferentially spaced from one another and interposed by a circumferential discontinuity. In a more detailed embodiment, the first opening of the first washer is partially defined by four threaded wall segments, each of the threaded wall segments being circumferentially spaced from one another by a separate circumferential discontinuity. In a more detailed embodiment, each circumferential discontinuity is defined by an axially inset wall of the first washer having a U-shaped cross-section, wherein the discontinuity is adapted to receive a driver. In another more detailed embodiment, the longitudinal threaded shaft of the screw includes threads having a first pitch and a first thread depth, the threaded head of the screw includes threads having a second pitch and a second thread depth, the first pitch is greater than the second pitch, and the first thread depth is greater than the second thread depth. In yet another more detailed embodiment, the base of the threaded head of the screw is tapered and the tapered surface is generally smooth.

In a more detailed embodiment of the second aspect, the second opening of the second washer is at least partially defined by a rounded over surface extending between a horizontal top surface and a wall predominantly defining the second opening, in yet another more detailed embodiment, the threaded head of the screw includes a spherical exterior surface. In a further detailed embodiment, the invention further includes a third washer defining a third opening and being insertable into the through hole, the third washer includes a widthwise dimension substantially greater than a thickness. In still a further detailed embodiment, the third washer is a spring washer. In a more detailed embodiment, the third washer comprises at least one of a helical washer, a Belleville washer, a wave spring washer, and a helical coil. In a more detailed embodiment, the through hole of the plate material includes at least two cutouts extending vertically into the semispherical wall, but not completely through the plate material, the at least two cutouts being oriented horizontally across from one another. In another more detailed embodiment, the at least two cutouts include a widthwise dimension greater than the cumulative total thickness of the first washer, the second washer, and the third washer.

It is a third aspect of the present invention to provide a method of locking a screw in any one of a plurality of possible angular orientations with respect to a plate material, the method comprising: (a) inserting a screw through corresponding openings of a first washer and a second washer seated within a through hole of a plate material: and (b) rotating the screw to increase a vertical distance between the first washer and the second washer to lock an orientation of the screw in one of a plurality of possible axial orientations.

In a more detailed embodiment of the third aspect, the act of rotating the screw includes engaging threads on a head of the screw with threads on a hole extending through the first washer. In yet another more detailed embodiment, the at least two washers remain within the through hole of the plate material while the screw is rotated. In a further detailed embodiment, the act of inserting the screw includes inserting a longitudinal shaft of the screw through the corresponding openings of the pair of washers, and the act of rotating the screw includes rotating a head of the screw to engage at least one of the openings of the pair of washers to vertically reposition the at least one of the washers along a length of the screw. In still a further detailed embodiment, the through hole of the plate material is at least partially defined by a semispherical wall segment, and the through hole at least partially includes at least two cutouts extending into the semispherical wall segment, the at least two cutouts being oriented horizontally across from one another. In a more detailed embodiment, inserting the first washer and the second washer into the through hole of the plate material prior to the act of inserting the screw. In a more detailed embodiment, inserting the screw through a corresponding opening of a third washer seated within a through hole of a plate material, where the third washer interposes the first washer and the second washer when within the through hole. In another more detailed embodiment, the third washer comprises at least one of a helical washer, a Belleville washer, a wave spring washer, and a helical coil. In yet another more detailed embodiment, the method further includes the act of biasing the first washer and the second washer against a wall of the plate material defining the through hole to retard axial and rotational repositioning of the first washer and second washer with respect to the plate material. In still another more detailed embodiment, the act of biasing the first washer and the second washer against the wall of the plate material includes interposing a third washer between the first and second washers.

In yet another more detailed embodiment of the third aspect, the third washer comprises at least one of a helical washer, a Belleville washer, a wave spring washer, and a helical coil. In still another more detailed embodiment, the act of biasing the first washer and the second washer against the wall of the plate material includes forming deformable prongs on at least one of the first washer and the second washer, where the deformable prongs exhibit a predetermined spring force. In a further detailed embodiment, the act of inserting the screw through corresponding openings of the first washer and the second washer includes the screw contacting the first washer and the second washer to overcome the bias and allow rotational and axial repositioning of the first washer and the second washer with respect to the plate. In still a further detailed embodiment, the act of inserting the screw through corresponding openings of the first washer and the second washer includes engaging threads on a head of the screw with thread partially defining the corresponding opening of the first washer, the act of rotating the screw includes rotating the threads of the head of the screw with respect to the threads partially defining the corresponding opening of the first washer to vertically reposition the first washer along a length of the screw, and the act of rotating the screw includes rotating a shaft of the screw within the corresponding opening of the second washer. In a more detailed embodiment, the act of rotating the screw to increase the vertical distance between the first washer and the second washer includes abutting the head of the screw against the first washer to maintain an axial position of the second washer with respect to the screw.

It is a fourth aspect of the present invention to provide a locking screw assembly comprising: (a) a plate material having a through hole at least partially defined by a semispherical wall segment: (b) a first washer including threads at least partially defining a first opening extending between a top surface and a bottom surface, the first washer having a fixed circumferential dimension and being insertable into the through hole; (c) a screw including a longitudinal threaded shaft extending from a threaded head, the longitudinal threaded shaft being sized to pass unimpeded through the first opening of the first washer, the threaded head being sized to engage the threads of the first washer to provide for longitudinal movement of the first washer along a length of the screw, where the first opening is sized to allow throughput of the longitudinal threaded shaft, and where the semispherical wall segment is sized to retain the first washer within the through hole.

In a more detailed embodiment of the fourth aspect, the invention further comprises a second washer including a second opening extending between a top surface and a bottom surface, the second washer having a fixed circumferential dimension and being insertable into the through hole, where the second opening is sized to allow throughput of the longitudinal threaded shaft, where the second opening is sized to prohibit throughput of the threaded head, and where the semispherical wall is sized to retain the first washer and the second washer within the through hole. In yet another more detailed embodiment, the invention further comprises a driver including a first engagement device and a second engagement device, wherein the first engagement device is rotatably repositionable with respect to the second engagement device. In a further detailed embodiment, at least one of the first washer and the second washer is discontinuous, in still a further detailed embodiment, the semispherical wall segment of the plate material includes a widthwise dimension greater than a vertical dimension. In a more detailed embodiment, the through hole of the plate material includes at least two cutouts extending into the semispherical wall, the at least two cutouts being oriented horizontally across from one another. In a more detailed embodiment, the at least two cutouts are both oriented on the same side of a horizontal diametric chord of the through hole. In another more detailed embodiment, at least one of the first washer and the second washer includes a rounded circumferential surface interposing the top surface and the bottom surface. In yet another more detailed embodiment, the rounded circumferential surface is at least one of smooth and textured. In still another more detailed embodiment, at least one of the first washer and the second washer includes a sloped circumferential surface interposing the lop surface and the bottom surface.

In yet another more detailed embodiment of the fourth aspect, the sloped circumferential surface is at least one of smooth and textured. In still another more detailed embodiment, a wall at least partially defining the second opening of the second washer is threaded. In a further detailed embodiment, the first opening of the first washer is partially defined by at least threaded wall segments, each of the threaded wall segments being circumferentially spaced from one another and interposed by a circumferential discontinuity. In still a further detailed embodiment, each circumferential discontinuity is defined by an axially inset wall of the first washer, wherein the discontinuity is adapted to receive a driver. In a more detailed embodiment, the first opening of the first washer is partially defined by four threaded wall segments, each of the threaded wall segments being circumferentially spaced from one another by a separate circumferential discontinuity. In a more detailed embodiment, each circumferential discontinuity is defined by an axially inset wall of the first washer having a U-shaped cross-section, wherein the discontinuity is adapted to receive a driver. In another more detailed embodiment, the longitudinal threaded shaft of the screw includes threads having a first pitch and a first thread depth, the threaded head of the screw includes threads having a second pitch and a second thread depth, she first pitch is greater than the second pitch, and the first thread depth is greater than the second thread depth. In yet another more detailed embodiment, a base of the threaded head, which interposes the threads of the head and the threads of the longitudinal shaft, is tapered and is generally smooth.

In yet another more detailed embodiment of the fourth aspect, the second opening of the second washer is at least partially defined by a rounded over surface extending between a horizontal top surface and a wall predominantly defining the second opening. In still another more detailed embodiment, the threaded head of the screw includes a spherical exterior surface. In a further detailed embodiment, the invention further includes a third washer defining a third opening and being insertable into the through hole, the third washer includes a widthwise dimension substantially greater than a thickness. In still a further detailed embodiment, the third washer is a spring washer. In a more detailed embodiment, the third washer comprises at least one of a helical washer, a Belleville washer, a wave spring washer, and a helical coil. In a more detailed embodiment, the through hole of the plate material includes at least two cutouts extending vertically into the semispherical wall, but not completely through the plate material, the at least two cutouts being oriented horizontally across from one another. In another more detailed embodiment, the at least two cutouts include a widthwise dimension greater than the cumulative total thickness of the first washer, the second washer, and the third washer.

It is a fifth aspect of the present invention to provide a locking screw assembly comprising: (a) a plate material having a through hole at least partially defined by a semispherical wall; (b) a first washer having a first through opening and occupying at least a first portion of the through hole: (c) a second washer having a second through opening and occupying at least a second portion of the through hole, the second washer being seated upon the semispherical wall: (d) a spring interposing the first washer and the second washer, the spring including a third through opening and occupying at least a third portion of the through hole; and (e) a locking screw including a longitudinal threaded shaft and occupying at least a fourth portion of the through hole.

In a more detailed embodiment of the fifth aspect, the spring comprises at least one of a helical washer, a Belleville washer, a wave spring washer, and a helical coil.

BRIEF DESCRIPTION OF THE DRAWINGS

FIG. 9 is a profile view of an exemplary screw comprising part of the variable angle locking screw assembly of FIG. 1.

FIG. 10 is an elevated perspective view of the exemplary screw of FIG. 9.

FIG. 11 is a profile view of an exemplary tool for use with the variable angle locking screw assembly of FIG. 1.

FIG. 12 is an elevated perspective view of a distal end of the exemplary tool of FIG. 11.

FIG. 38 is a bottom view of another washer comprising part of a fourth exemplary variable angle locking screw assembly.

DETAILED DESCRIPTION

The exemplary embodiments of the present disclosure are described, and illustrated below to encompass methods and associated devices for positioning and locking the orientation of a variable angle screw. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
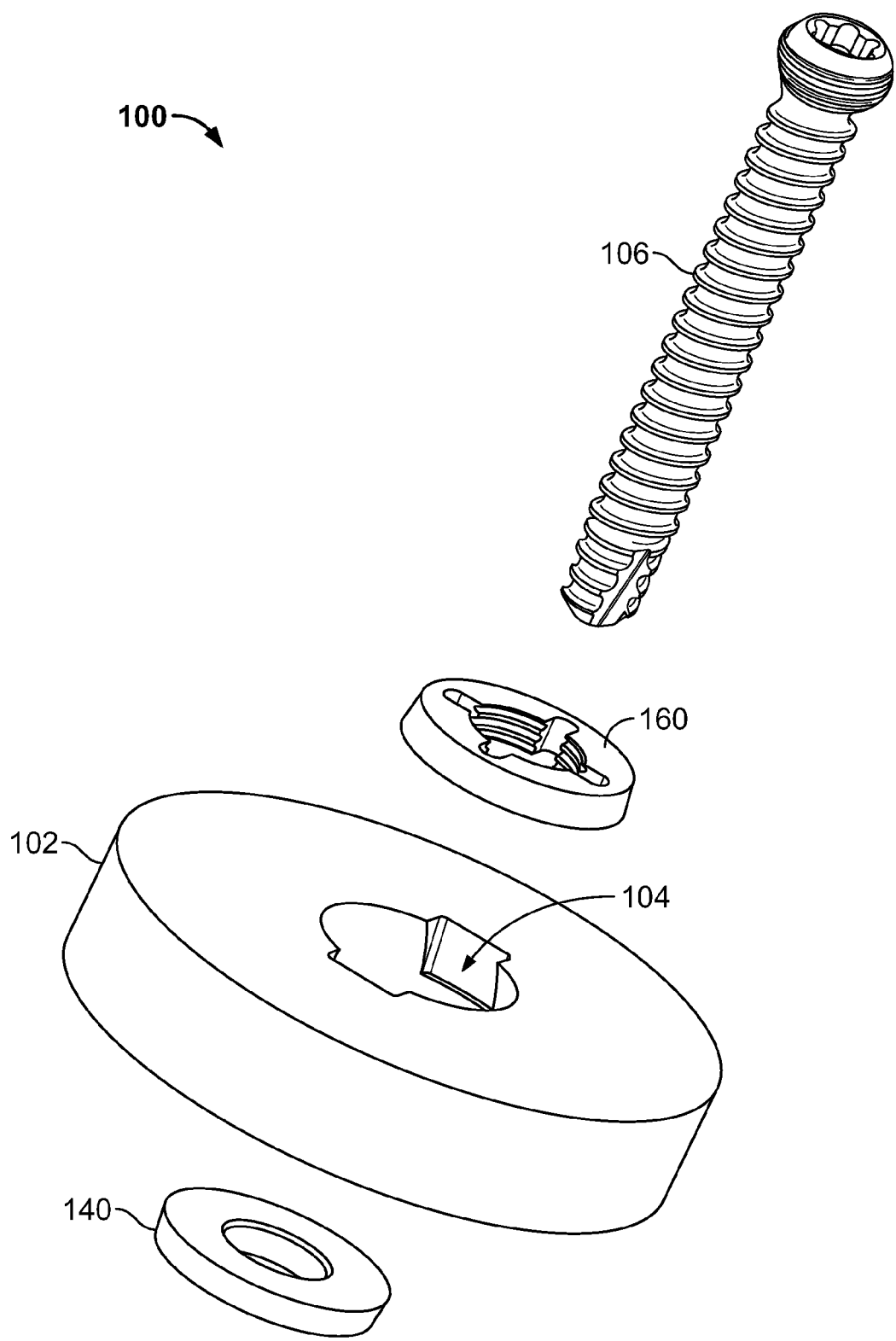
FIG. 1 is an exploded view of a first exemplary variable angle locking screw assembly.

Referencing FIG. 1, an exemplary variable angle locking screw assembly 100 includes a plate material 102 having one or more through holes 104, with each through hole adapted to receive a screw 106 that mounts the plate material to bodily tissue such as, without limitation, bone (not shown). Because the plate material 102 may not always be planar, there may be instances where the surgical screw 106 is oriented at an angle other than perpendicular with respect to a vertical axis of the through hole (or with respect to the bottom and top surfaces of the plate material). And these angular orientations and rotational orientations may vary, so it is advantageous to provide flexibility as to the angular and rotational orientations of the screw 106.

Figure 2:
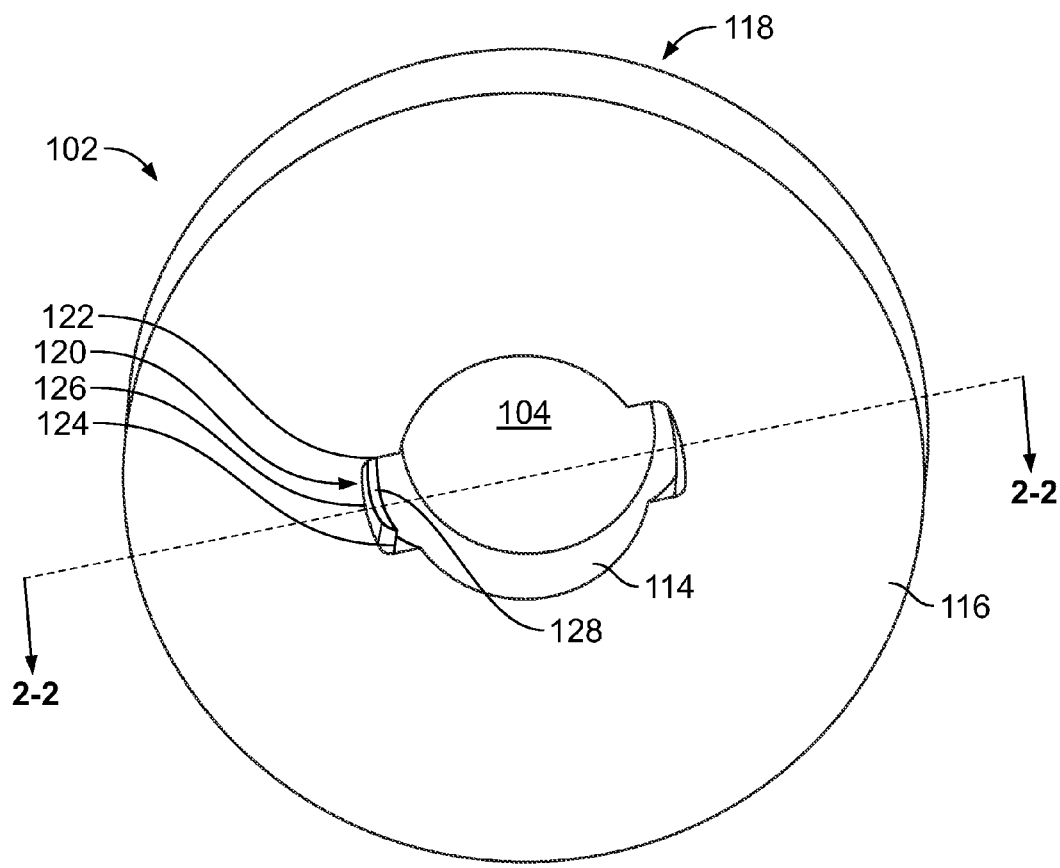
FIG. 2 is an elevated perspective view from the top of an exemplary plate material comprising part of the variable angle locking screw assembly of FIG. 1.
Figure 3:
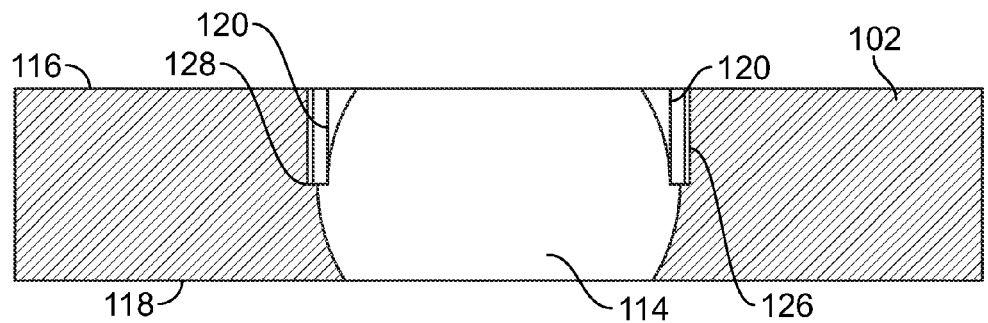
FIG. 3 is a cross-sectional view of the exemplary plate material of FIG. 2 taken along lines 2-2.

Referring to FIGS. 1-3, a number of walls define the through hole 104 in the plate material 102. These walls include a semi-spherical wall 114 that demarcates the majority of the through hole 104, where the semi-spherical wall extends between the top and bottom surfaces 116, 118 of the plate material 102. In this exemplary embodiment, the semi-spherical wall 114 may be smooth or textured. A pair of cutouts 120 extends into the semi-spherical wall 114 and, as will be discussed hereafter, cooperates to provide a widthwise opening sufficiently sized to insert a pair of washers 140, 160 into the through hole. The cutout 120 is partially demarcated by a pair of opposing vertical walls 122, 124 that extend from the top surface 116 and define a lateral dimension of the cutout. The opposing vertical walls 122, 124 cooperate with an adjoining, perpendicular side wall 126 that also extends from the top surface 116 and gives the cutouts a block C-shaped vertical profile. The cutouts 120 vertically extend just beneath the vertical midpoint of the through hole 104 and include a horizontal floor 128 that provides a ledge.

Consistent with the dimensions of the semi-spherical wall 114, the dimensions of horizontal cross-sections of the through hole 104 is not constant along the vertical length of the through hole (i.e., between the top and bottom surfaces 116, 118). As discussed above, the cutouts 120 disrupt the arcuate, vertical nature of the semi-spherical wall 114. The consistent arc segments (of the horizontal cross-sections) that are interposed by the profiles of the cutouts 120 would otherwise form complete circular rings. Accordingly, but for the presence of the cutouts 120, the semi-spherical wall 114 could be thought of as a series of circular rings stacked upon one another, where the rings did not all embody a constant diameter.

In exemplary form, the arc segments or rings taken from the horizontal cross-section of the through hole 104 at the top and bottom surfaces 116 of the plate material 102 provide a different circular diameter than the arc segments taken from the horizontal cross-section of the through hole at the vertical midpoint between the top and bottom surfaces. In other words, in exemplary form, the rings or arcs at the top and bottom surfaces 116, 118 that define a portion of the semi-circular wall 114 have the smallest diameter, while the arcs at the vertical midpoint of the through hole have the largest diameter. Consequently, the diameter of the circular rings or arcs progressively change as one vertically moves along the semi-spherical wall 114. This progressive change in the diameter of the rings and arcs gives the semi-spherical wall 114 its arcuate, vertical profile. In this exemplary embodiment, the diameter of the through hole 104 at the top and bottom surfaces 116, 118 is generally the same, but for the cutouts 120. However, as will be understood by those skilled in the art, it is not required that the diameter of the through hole 104 at the top and bottom surfaces 116, 118 be identical.

Figure 4:
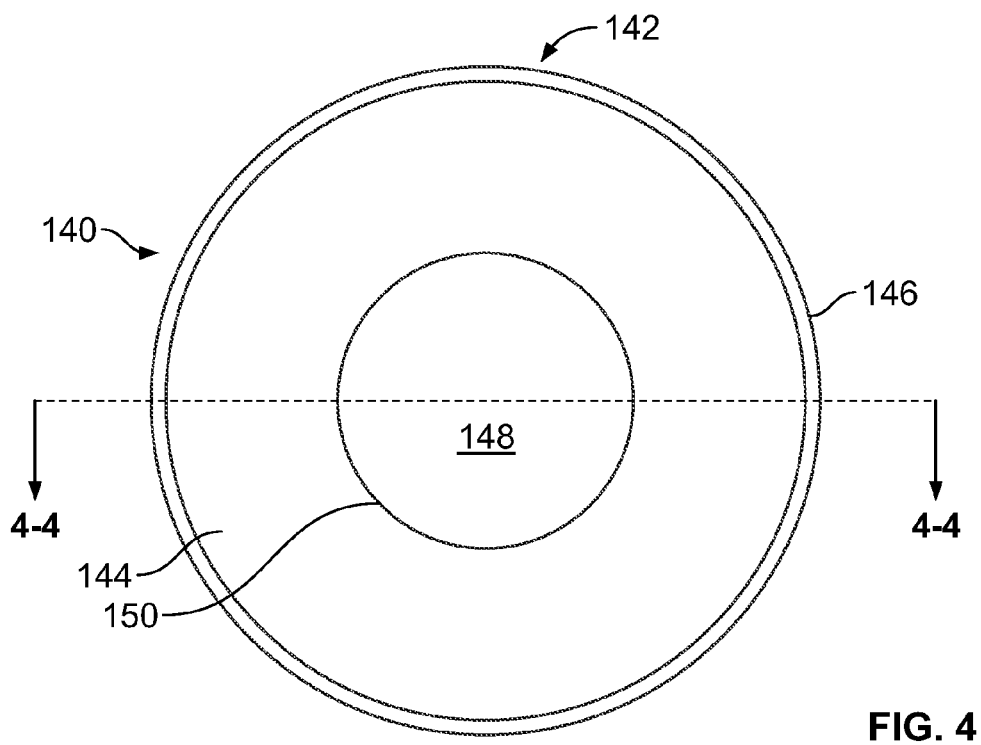
FIG. 4 is a bottom view of an exemplary washer comprising part of the variable angle locking screw assembly of FIG. 1.
Figure 5:
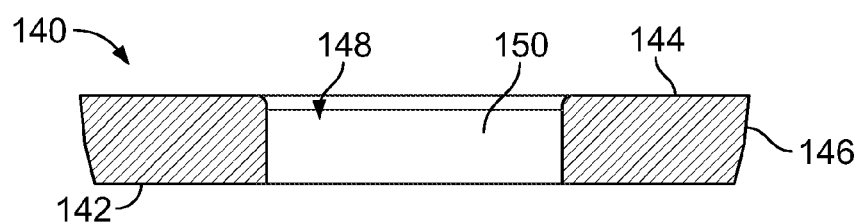
FIG. 5 is a cross-sectional view of die exemplary washer of FIG. 4 taken along lines 4-4.

Referencing FIGS. 1, 4, and 5, the exemplary variable angle locking screw assembly 100 includes a first washer 140 having a generally planar top surface 142 spaced apart from a generally planar bottom surface 144. An outermost circumferential surface 146 of the washer 140 is arcuate (or tapered from top to bottom 142, 144) and extends between the top and bottom surfaces 142, 144 to delineate the horizontal widthwise dimension of the washer, where the widthwise dimension at the bottom surface is less than the widthwise dimension at the top surface. This circumferential surface 146 may be smooth or textured so as to change the fractional characteristics of the surface with respect to the semi-spherical wall 114 of the plate material 102. Inset and centered with respect to the circumferential surface 146 is a through hole 148 bounded by a cylindrical surface 150 having a constant diameter. In this exemplary embodiment, the interface between the top surface 142 and the cylindrical surface 150 is rounded over to better approximate the contour of the bottom surface of the screw 106.

Figure 6:
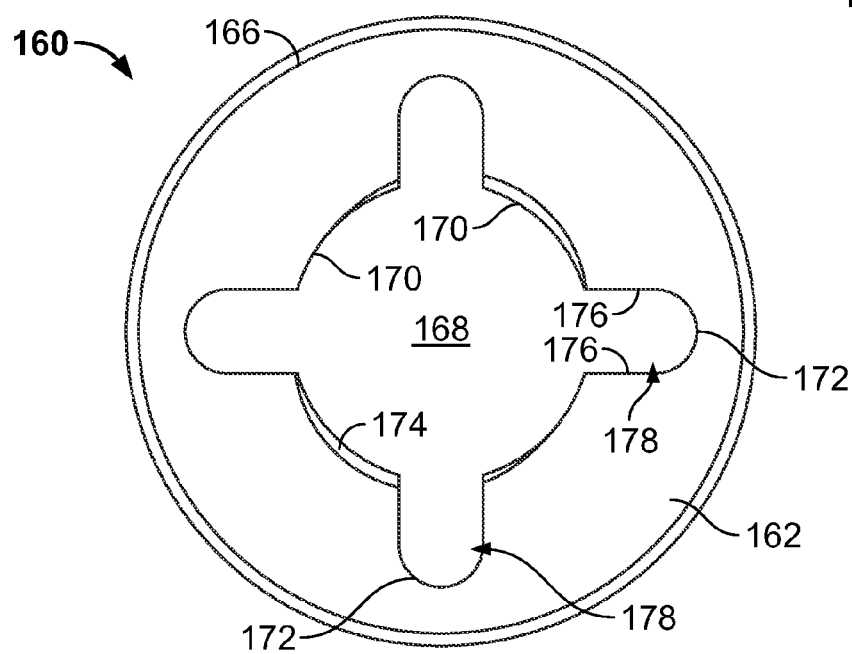
FIG. 6 is a lop view of an exemplary washer comprising pan of the variable angle locking screw assembly of FIG. 1.
Figure 7:
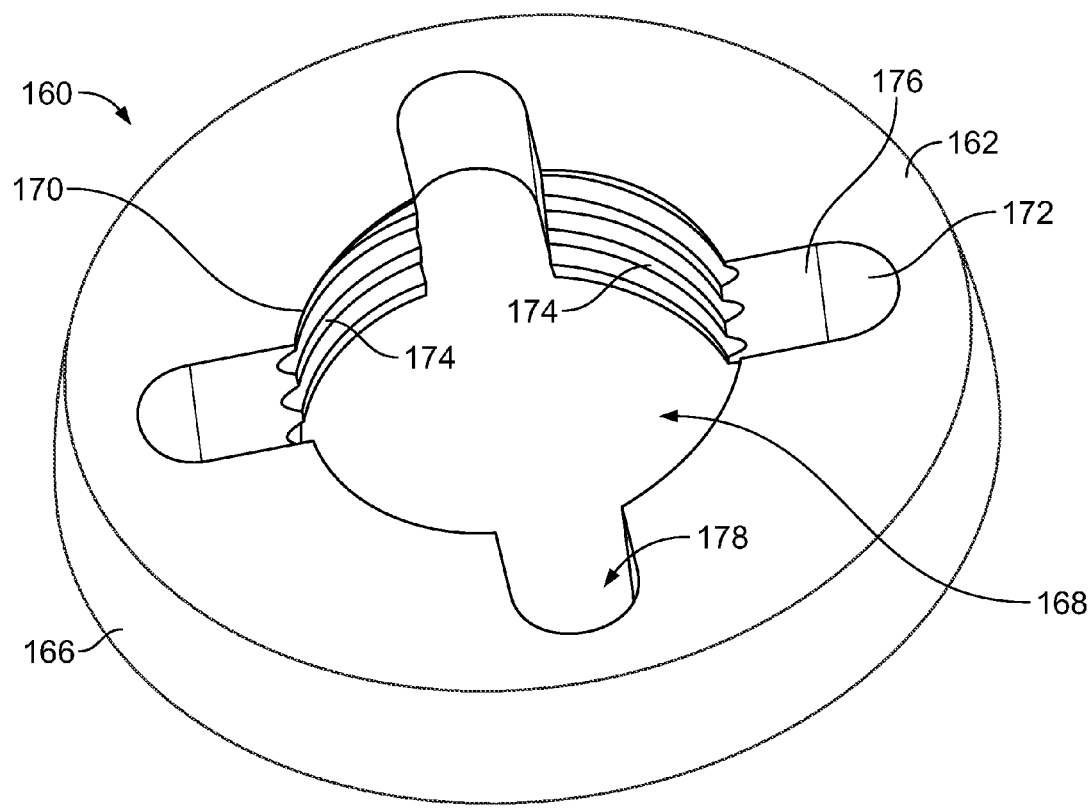
FIG. 7 is an elevated perspective view of the exemplary washer of FIG. 6.
Figure 8:
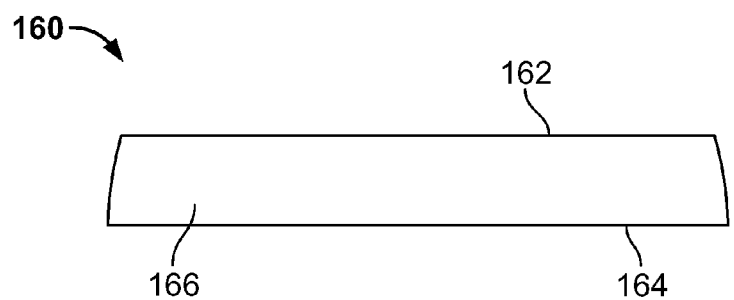
FIG. 8 is a profile view of the exemplary washer of FIG. 6.
Figure 13:
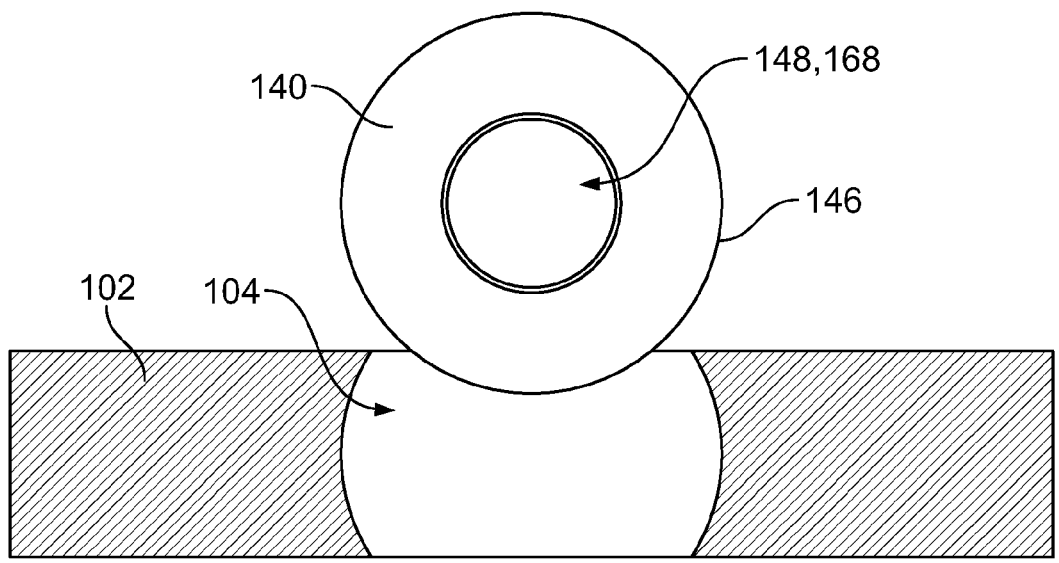
FIG. 13 is a cross-sectional view of the exemplary plate material of FIG. 3, just prior to vertical insertion of the washers of FIGS. 4 and 6.

Referring to FIGS. 6-8, the exemplary variable angle locking screw assembly 100 also includes a second washer 160 having a generally planar top surface 162 spaced apart from a generally planar bottom surface 164. An outermost circumferential surface 166 of the washer 160 is arcuate (or tapered from bottom to top 164, 162) and extends between the top and bottom surfaces 162, 164 to delineate the horizontal widthwise dimension of the washer, where the widthwise dimension at the bottom surface is greater than the widthwise dimension at the top surface. The circumferential surface 166 of the washer 160 may be smooth or textured so as to change the frictional characteristics of the surface with respect to the semi-spherical wall 114 of the plate material 102. Inset and centered with respect, to the circumferential surface 166 is a through hole 168 partially bounded by four arcuate surfaces 170 and four partial cylindrical surfaces 172. Each of the arcuate surfaces 170 includes threads 174 and corresponding recesses adapted to establish a threaded connection with the screw 106. A series of planar surfaces 176 link the partial cylindrical surfaces 172 with the arcuate surfaces 170 that collectively define the through hole 168. Each of the partial cylindrical surfaces 170, 172 and planar surfaces 176 is oriented generally perpendicular to the top and bottom surfaces 162, 164. These planar surfaces 176 cooperate with the partial cylindrical surfaces 172 to delineate four recesses 178 radially extending from the center of the through hole 168.

Referencing FIGS. 9 and 10, the screw 106 of the exemplary variable angle locking screw assembly 100 includes a head 180 and an elongated shaft 182 extending from the head. The head 180 is generally circular in horizontal cross-section and includes a substantially planar top surface 184 spaced apart from a conical bottom surface 186 that tapers and narrows in diameter as the distance from the top surface increases. A circumferential surface 188 of the head 180, which extends between the top and bottom surfaces 184, 186, is substantially smooth but for helical threads 190 that extend around the circumference of the head. This circumferential surface 188 in combination with the threads 190 delineates the horizontal widthwise dimension of the screw head 180. More specifically, the horizontal widthwise dimension of the screw head 180 is larger than the horizontal widthwise dimension of the elongated shaft 182. An opening 192 extends from the top surface 184 normally into the interior of the head 180 and is bounded by six vertical walls 194 and six partial cylindrical walls 196 that are oriented in an alternating pattern. The walls 194, 196 intersect a conically depressed floor 198. The conical floor 198 extends partially into the interior of the elongated shaft 182, which extends normally from the bottom surface 186 of the head 180. The elongated shaft 182 is generally cylindrical in horizontal cross-section and includes helical threads 200 distributed about its circumference from proximate the bottom surface 186 of the head 180 to the tip 202 of the elongated shaft, which includes conical portion 204 transitioning from the generally circular cross-section of the elongated shaft to the tip. It should be noted that the horizontal widthwise dimension of the head 180 is substantially larger than the widthwise dimension of the elongated shaft 182 so that the bottom surface 186 of the head that extends laterally outward (i.e., widthwise) beyond the elongated shaft provides a conical plateau.

Referring to FIGS. 11 and 12, an exemplary tool 210 for use with the variable angle locking screw assembly 100 includes an outer housing 212 defining a cylindrical bore occupied by an inner shaft 214 that is longitudinally and rotatably repositionable with respect to the outer housing. The distal end 216 of the outer housing 212 includes four projections 218 evenly spaced and oriented in a circular pattern. In this exemplary embodiment, each projection 218 includes an outer arcuate surface 220 spaced apart from an inner arcuate surface 222 by two planar side surfaces 224 and a bottom surface 226. As will be discussed in more detail below, the projections 218 are adapted to be received within the recesses 178 of the second washer 160 in order to inhibit rotation of the washer with respect to the inner shaft 214. At a distal end 228 of the inner shaft 214 is a hexagonal driver 230 having six vertical sidewalls 232 and a substantially planar bottom surface 234. Again, as will be discussed in more detail below, the driver 230 is adapted to be received within the opening 192 of the screw head 180 in order to rotate of the screw 106 with respect to the outer housing 212 and the second washer 160.

Referring to FIGS. 13-17, assembling the variable angle locking screw assembly 100 includes orienting the plate material 102 so that the through hole 104 is accessible. Thereafter, both washers 140, 160 are grasped and oriented so that the top surface 142 of the first washer 140 is adjacent the bottom surface 164 of the second washer 160, with the through holes 148, 168 being generally aligned to overlap one another. At the same time, the circumferential surfaces 146, 166 of the washers 140, 160 are oriented to generally overlap one another. After placing the washers 140, 160 in an adjacent orientation as discussed above, the washers are vertically oriented so that the washers lie on their respective sides. This allows the washers to be lowered into the through hole 104 of the plate material 102. Specifically, the thickness (straight line distance between the top and bottom surfaces of the washers) of both washers 140, 160 is less than the straight line distance between the opposing vertical walls 122, 124 of the plate material 102, thereby allowing the washers to pass into the through hole 104 and between the opposing vertical walls until the circumferential surfaces 146, 166 reaching the ledge 128.

Figure 14:
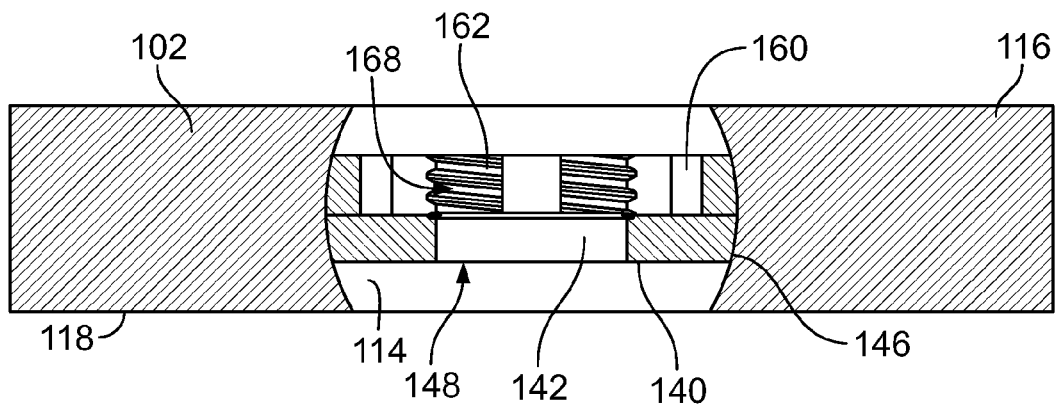
FIG. 14 is a cross-sectional view of the exemplary plate material of FIG. 3, just after vertical insertion and ninety degree turning of the washers of FIGS. 4 and 6.

Looking to FIG. 14, after the washers 140, 160 have been lowered into the through hole 104 and in between the opposing vertical walls 122, 124 of the plate material 102 to contact the ledge 128, the washers are rotated approximately 90 degrees to lye flat so that the second washer 160 lies on top of the first washer 140. More specifically, the washers 140, 160 when rotated are oriented so that the top surfaces 142, 162 of the washers are parallel to the top surface 116 of the plate material 102. As a result, the widthwise dimension of the first washer 140, upon which the second washer 160 is seated, is greater than the diameter of the semi-spherical wall 114 proximate the bottom surface 118 of the plate material 102. Accordingly, the first washer 140 sits upon the semi-spherical wall 114. But when the washers 140, 160 are oriented vertically or within thirty degrees of vertical and aligned with the opposing vertical walls 122, 124 of the plate material 102, the thickness of the washers 140, 160 allows the washers to be similarly removed from the through opening. However, when in use, while the screw 106 is inserted through the opening 104 and holes 148, 168 in the washers 140, 160, thereby restricting the washers 140, 160 from being oriented vertically or within thirty degrees of vertical.

Figure 15:
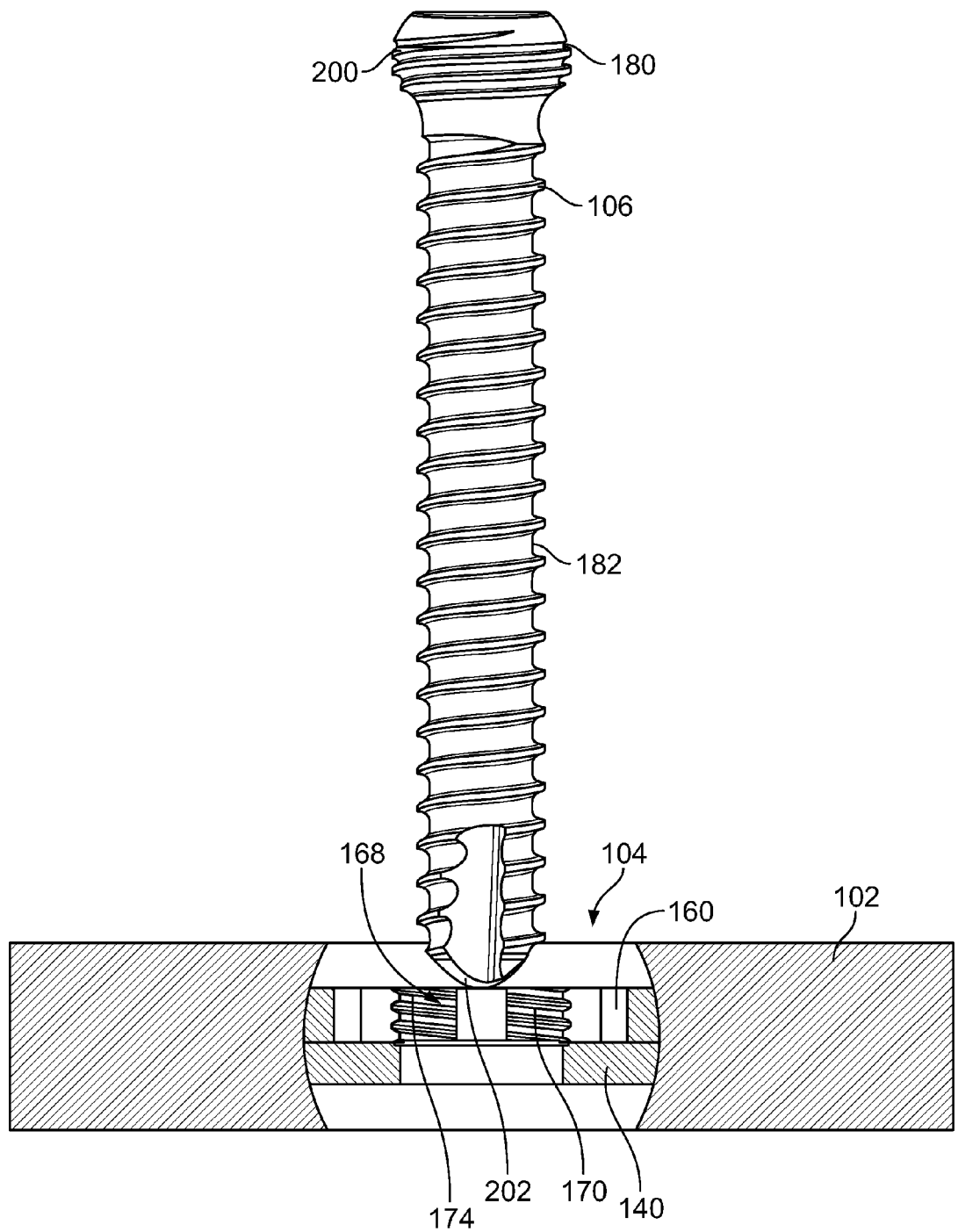
FIG. 15 is a cross-sectional view of the exemplary plate material of FIG. 3, subsequent to insertion of the washers of FIGS. 4 and 6, but just prior to insertion of the exemplary screw of FIG. 9.

Next, viewing FIG. 15, after the washers 140, 160 have been horizontally oriented within the through hole 104, the screw 106 is inserted into the through hole with the tip 202 of the elongated shaft 182 being inserted prior to the screw head 180. Because the widthwise dimensions of the through opening 104 and the openings 148, 168 of the washers is substantially larger than the widthwise dimension of the screw shaft 182, the shaft passes through the plate material 102, the first washer 140 and the second washer 160 without constraint. However, the central portion of the opening 148 of the first washer 140 is smaller in cross-section than the screw head 180. As a result, while the elongated shaft 182 passes through first washer 140, the screw head 180 is inhibited from passing through the first washer. Similarly, the circular portion of the hole 168 of the second washer 160, defined by the arcuate surfaces 170, is approximately the same horizontal dimension as that of the screw head 180 and thereby retards the screw head from passing through the second washer until the screw head is rotated with respect to the second washer so the threads 174, 200 can engage one another. More specifically, the threads 174 of the arcuate surfaces 170 are adapted to engage the threads 200 of the screw head 180 to allow the second washer 160 to vertically travel along the screw head as the screw is rotated with respect to the second washer. Consequently, when the elongated shaft 182 of the screw 106 is initially inserted through the washers 140, 160, the threads 200 of the screw head 180 sit upon the threads 174 of the second washer.

Figure 16:
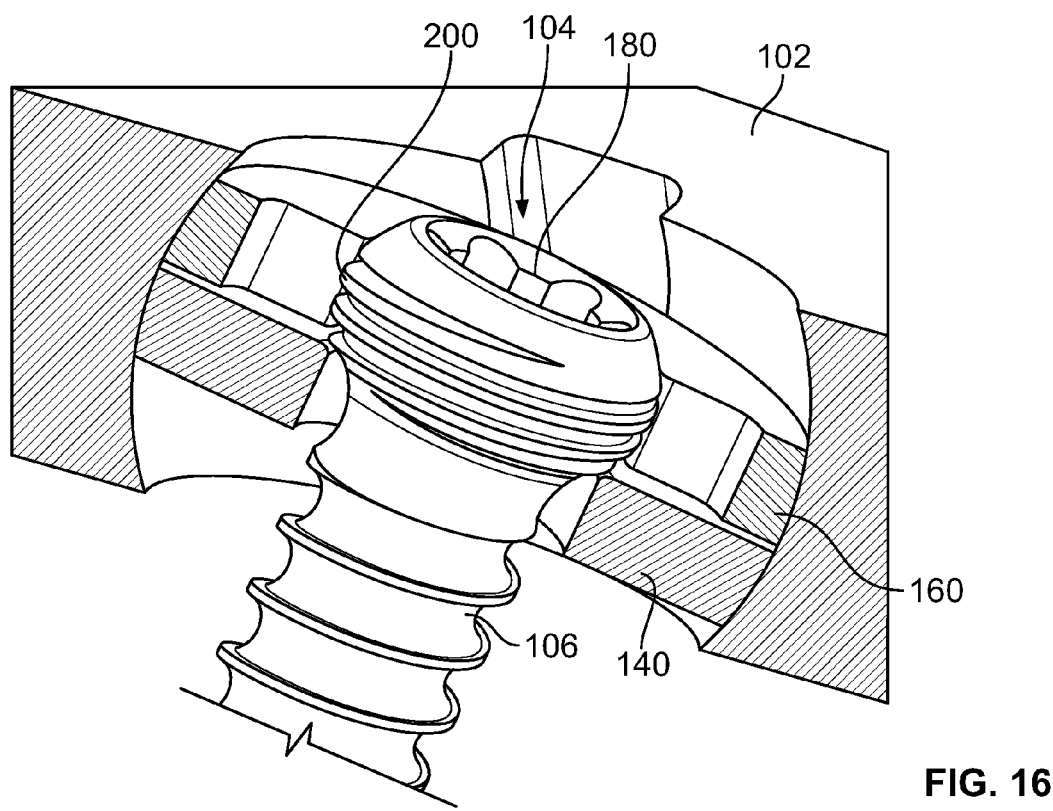
FIG. 16 is a cross-sectional view of the exemplary variable angle locking screw assembly of FIG. 1, prior to locking of the screw in a fixed orientation.

With reference to FIG. 16, the distal end 216 the tool 210 is inserted into the lop of the through hole 104 to engage the screw 106 and the second washer 160. Specifically, the projections 218 of the tool 210 are vertically aligned with the exposed recesses 178 of the second washer 160. It should be noted that the spacing and orientation of the projections 218 is generally the same as the spacing and orientation of the recesses 178 so that when aligned, the tool 210 may be vertically repositioned with respect to the second washer 160 so that the projections 218 are received within the recesses 178. Concurrent with repositioning of the projections 218 into the recesses 178 of the second washer 160, the driver 230 is also vertically repositioned into the opening 192 at the top of the screw head 180. But before the driver 230 is vertically repositioned into the opening 192, the driver must be rotationally aligned so that the six hexagonal vertical walls 232 are oriented in parallel to the six hexagonal vertical walls 194 circumferentially bounding the opening. After this alignment is achieved, the tool 210 is vertically repositioned farther into the through hole 104 so that the driver 230 is received within the opening 192 and the projections 218 are received within the recesses of the second washer 160. In this manner, the tool 210 is concurrently coupled to the screw 106 and the second washer 160.

At this point, while the washers 140, 160 are not wedged against the semi-spherical wall 114 of the plate material 102, the orientation of the screw 106 and washers is able to be modified axially up to thirty degrees from vertical in all 360 rotational degrees. But once the washers 140, 160 are wedged against the semi-spherical wall 114 of the plate material 102, the orientation of the screw 106 and washers becomes fixed or locked. Accordingly, the tool 210, after being concurrently coupled to the screw 106 and the second washer 160, is repositioned axially up to thirty degrees from vertical and rotationally in order to position the screw in the proper orientation. By repositioning the tool 210, which is concurrently coupled to the screw 106 and the second washer 160, the movement of the second washer is operative to reposition the first washer 140 to have essentially the same axial orientation as the second washer.

Once the desired orientation of the screw 106 is achieved, the tool 210 is utilized to rotate the screw 106 with respect to the second washer 160 in order to increase the distance between the washers 140, 160. Specifically, the inner shaft 214 of the tool 210 is rotated clockwise to rotate the driver 230 in a clockwise direction, while at the same time the outer housing 212 of the tool remains stationary or is rotated in a counterclockwise direction. The difference in relative rotation (i.e., opposite directions) between the screw 106 and the second washer 160 is operative to vertically reposition the second washer with respect to the screw as the threads 174, 190 of each component engage one another. In other words, clockwise rotation of the screw 106 with respect to the second washer 160 is operative to vertically raise the second washer with respect to the screw along the longitudinal axis of the screw. The vertical motion of the second washer 160 also increases the distance between the washers 140, 160 because the first washer 140 is not vertically repositioned as the screw 106 is rotated clockwise or counterclockwise. This is the case because the hole 168 through the first washer 140 is not large enough to accommodate the screw head 180, so the bottom surface 186 of the screw head acts as a camming surface against the top surface 142 of the first washer to maintain the vertical position of the screw 106 with respect to the first washer.

Figure 17:
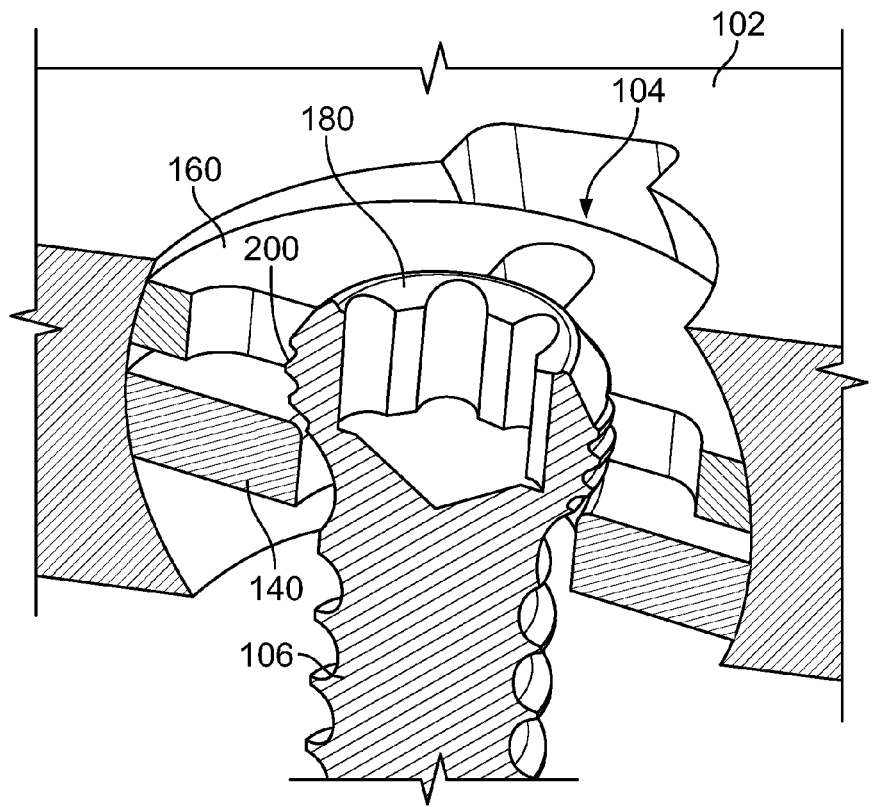
FIG. 17 is a cross-sectional view of the exemplary variable angle locking screw assembly of FIG. 1, subsequent to locking of the screw in a fixed orientation.
Figure 18:
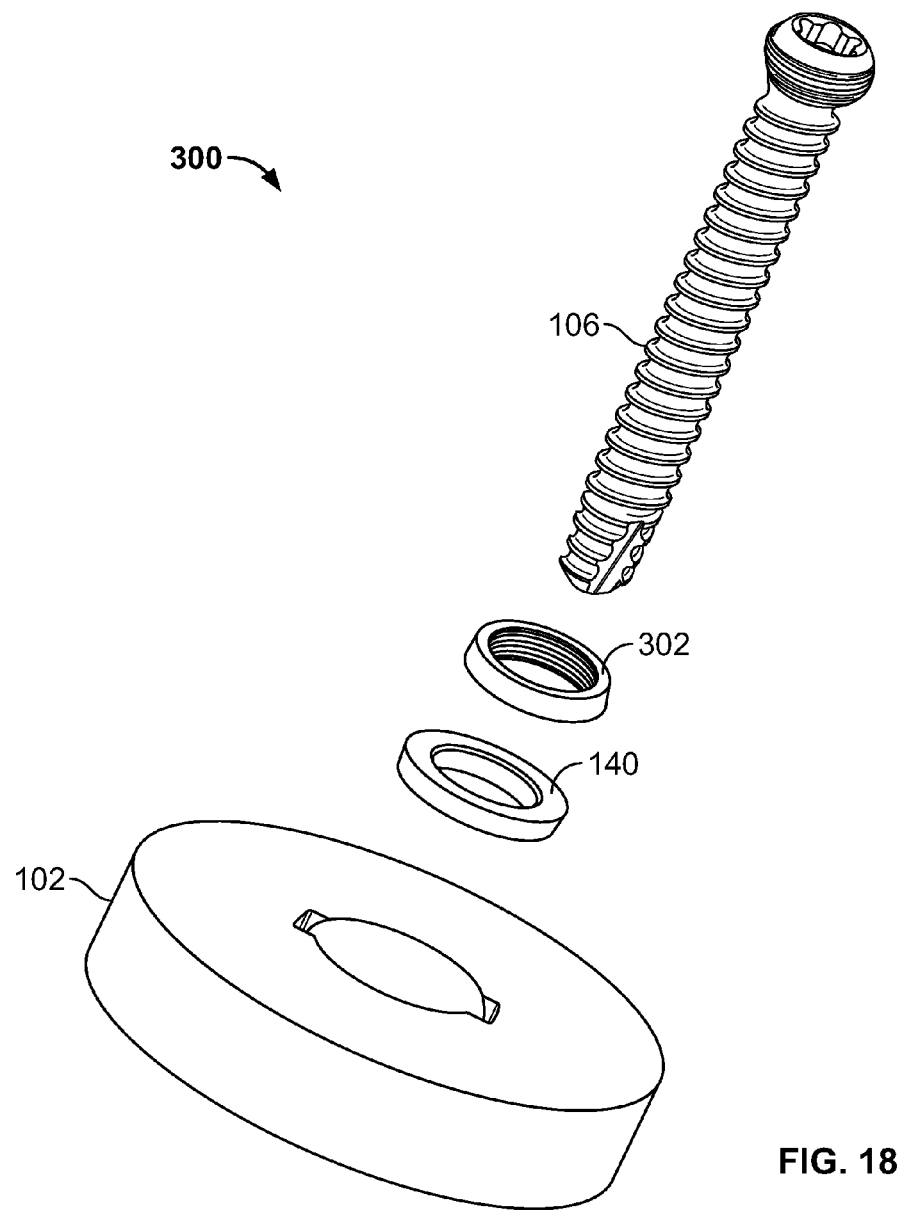
FIG. 18 is an exploded view of a second exemplary variable angle locking screw assembly.
Figure 19:
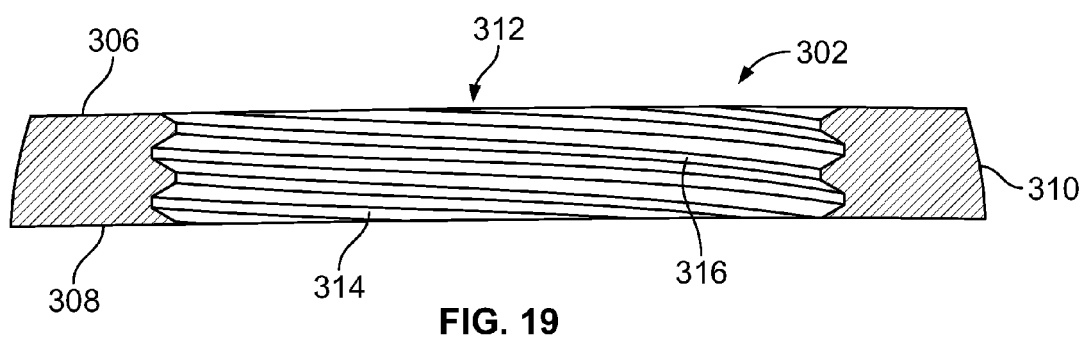
FIG. 19 is a cross-sectional view of the exemplary threaded washer of FIG. 18.
Figure 20:
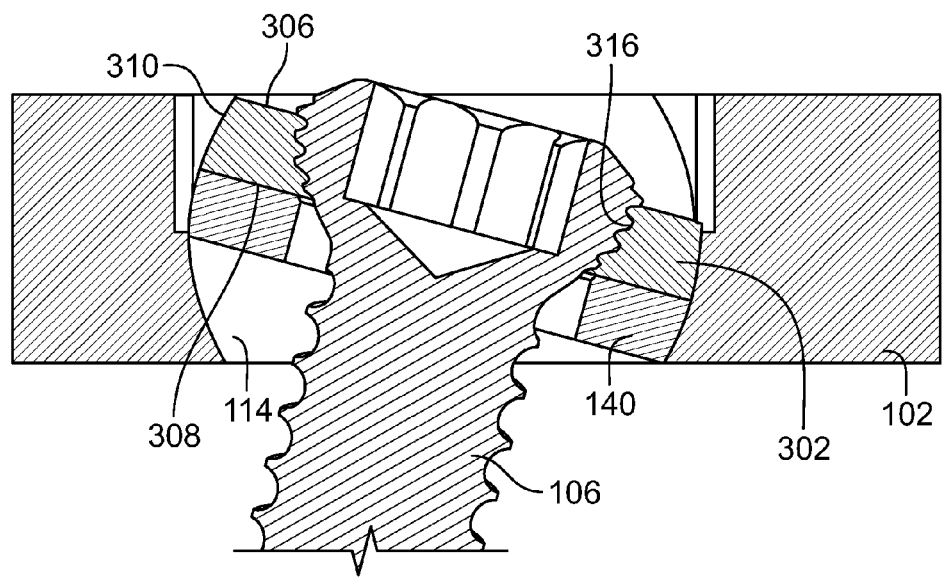
FIG. 20 is it cross-sectional view of the exemplary variable angle locking screw assembly of FIG. 18, prior to locking of the screw in a fixed orientation.
Figure 21:
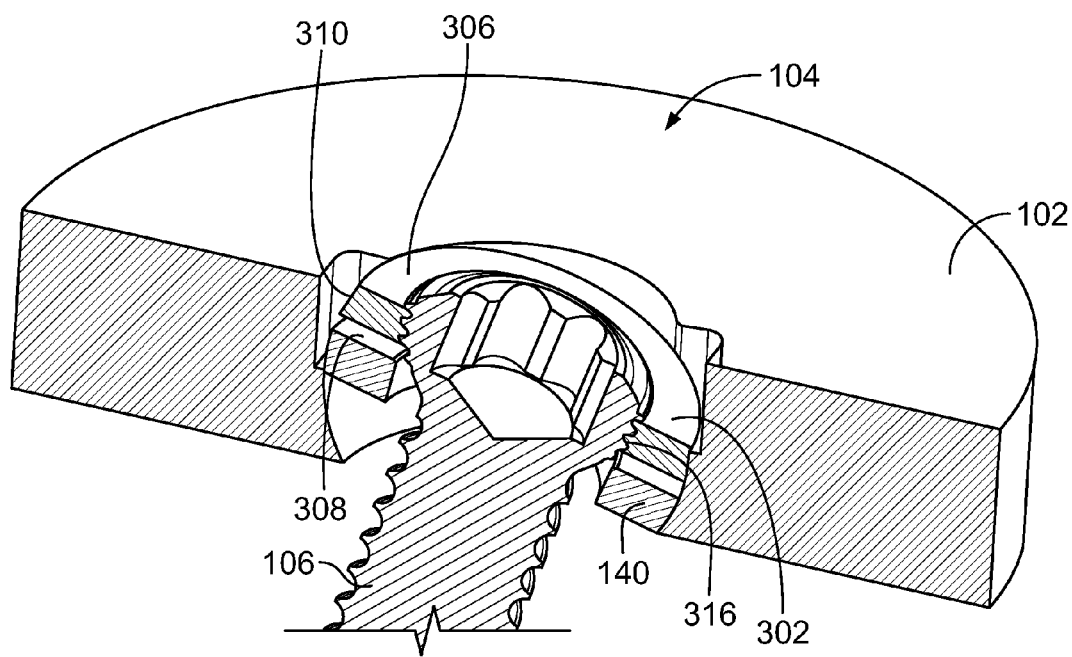
FIG. 21 is a cross-sectional view of the exemplary variable angle locking screw assembly of FIG. 18, subsequent to locking of the screw in a fixed orientation.

Referencing FIG. 17, eventually the second washer 160 is repositioned vertically so that the outermost circumferential surface 166 contacts the semi-spherical wall 114 of the plate material 102 to wedge the washers 140, 160 in position. Prior to this point, rotation of the screw 106 has been operative to concurrently push up on the second washer 160 while pushing down on the first washer 140 as the circumferential surfaces 146, 166 push against the semi-spherical wall 114 of the plate material 102, which creates a wedge between the washers 140, 160 and the plate material 102 to lock the axial and rotational orientation of the screw. As a result, further, limited clockwise rotation of the screw only creates a lighter wedge. Alter the wedge has been created, the tool 210 may be withdrawn from the through hole 104 because the wedge created between the washers 140, 160 and the semi-spherical wall 114 of the plate material 102 is operative to lock the axial and rotational orientation of the screw 106.

When the appropriate time is reached, the screw 106 may be repositioned by again inserting the tool 210 into the through hole 104. This includes vertically aligning the projections 218 of the tool 210 with the exposed recesses 178 of the second washer 160, in addition to aligning the driver 230 with respect to the screw opening 192. After this alignment is complete, the tool 210 is moved farther deeper into the through hole 104 so that the projections 218 are sealed within the recesses 178 and the driver 230 is received within the opening 192. Thereafter, the driver 230 is rotated in a counterclockwise direction with respect to the projections 218 and outer housing 212, which causes the screw 106 to rotate counterclockwise and discontinue the wedge fixing the axial and rotational orientation of the screw. Again, working backwards, counterclockwise rotation of the screw 106 causes the second washer 160 to be vertically repositioned along the screw head 180 so that the distance between the bottom surface 164 of the second washer and the top surface 142 of the first washer decreases.

At this point, the axial and/or rotational orientation of the screw 106 may be changed using the tool 210, followed by clockwise rotation of the screw to form a wedge locking the screw in a second, different orientation. Alternatively, the screw 106 may be completely removed from the through hole 104, which would include counterclockwise rotation of the screw until its threads 190 no longer engage the threads 174 of the second washer 160, thereby allowing the screw to be removed from the through hole 104. Though not required, removal of the screw 106 from the through hole 104 may also include removal of one or both of the washers 140, 160 from the through hole.

Referring to FIGS. 18-21, a second exemplary locking screw assembly 300 utilizes the same plate material 102 (with the exception of the semi-spherical wall 114 being textured, as opposed to smooth), the first washer 140, and the screw 106 from the first exemplary embodiment 100. What is different is that the second exemplary embodiment includes a different, second washer 302. As with the first exemplary embodiment 100, this second exemplary embodiment 300 allows for a plurality of axial and rotational orientations of the screw 106 and an ability to lock the screw in one of the plurality of orientations at a time. Because the same plate material 102, the same first washer 140, and the same screw 106 are used in this second exemplary embodiment 300, a more thorough discussion of these components with respect to this second exemplary embodiment has been omitted only for purposes of brevity.

The second washer 302 is adapted to be seated on the first washer 140 after being initially inserted into the through hole 104 and thereafter rotated ninety degrees. This second washer 302 includes a generally planar top surface 306 spaced apart from a generally planar bottom surface 308. An outermost circumferential surface 310 of the washer 302 is arcuate (or sloped) and extends between the top and bottom surfaces 306, 308 to delineate the widthwise dimension of the washer, where the widthwise dimension at the bottom surface is greater than the widthwise dimension at the top surface. The circumferential surface 310 of the washer is textured, though a smooth circumferential surface is also useful. Inset and centered with respect to the circumferential surface 310 is a through hole 312 partially bounded a cylindrical surface 314 that includes threads 316 adapted for establishing a threaded connection with the screw 106.

Referring again to FIGS. 18-20, assembling the second exemplary locking screw assembly 300 is very similar to that of the first exemplary embodiment in that the insertion of the washers 140, 302 is carried out in the same manner as the insertion previous washer set 140, 160. Accordingly, an explanation of insertion of the washers into the through hole 104 has been omitted only for purposes of brevity. Likewise, insertion of the screw 106 into the through hole 104 and into engagement with the second washer 302 is the same as that described in the first exemplary embodiment for the second washer 160. Consequently, an explanation of insertion of the screw 106 into the through hole 104 has also been omitted only for purposes of brevity.

After the washers 140, 302 have been inserted and positioned into the through hole 104, as well as the screw 106 being inserted into the through hole, the distal end of a driver (not shown) is inserted into the top of the through hole 104 to engage the screw 106. After alignment between the drive and screw is achieved, while the washers 140, 302 are not wedged against the semi-spherical wall 114 of the plate material 102, the orientation of the screw 106 and washers is able to be modified axially up to thirty degrees from vertical in all 360 rotational degrees. But once the washers 140, 302 are wedged against the semi-spherical wall 114 of the plate material 102, the orientation of the screw 106 and washers becomes fixed or locked. Accordingly, the driver, after being concurrently coupled to the screw 106, is repositioned axially up to thirty degrees from vertical and rotationally in order to position the screw in the proper orientation. By repositioning the driver, which is concurrently coupled to the screw 106, the movement of the second washer is operative to reposition the first washer 140 to have essentially the same axial orientation as the second washer.

Once the desired orientation of the screw 106 is achieved, the driver is utilized to rotate the screw 106 with respect to the second washer 302 in order to increase the distance between the washers 140, 302. Specifically, driver is rotated clockwise to rotate the screw 106 in a clockwise manner, while rotation of the second washer 302 is inhibited or retarded by friction while the driver is rotated. The difference in relative rotation (i.e., opposite direction) between the screw 106 and the second washer 302 is operative to vertically reposition the second washer with respect to the screw as the threads 316, 190 of each component engage one another. In other words, clockwise rotation of the screw 106 with respect to the second washer 302 is operative to vertically raise the second washer with respect to the screw along the longitudinal axis of the screw. The vertical motion of the second washer 302 also increases the distance between the washers 140. 302 because the first washer 140 is not vertically repositioned as the screw 106 is rotated clockwise or counterclockwise. This occurs, in part, because the hole 168 through the first washer 140 is not large enough to accommodate the screw head 180, so the bottom surface 186 of the screw head acts as a camming surface against the top surface 142 of the first washer to prohibit the screw head 180 from passing beyond the first washer.

Eventually, continued rotation of the screw 106 is operative to concurrently push up on the second washer 302 while pushing down on the first washer 140 as the circumferential surfaces 146, 310 push against the semi-spherical wall 114 of the plate material 102, which creates a wedge between the washers 140, 302 and the plate material 102 to lock the axial and rotational orientation of the screw. As a result, further, limited clockwise rotation of the screw only creates a tighter wedge. At this point, the driver may be withdrawn from the through hole 104 because the wedge created between the washers 140, 302 and the semi-spherical wall 114 of the plate material 102 is operative to lock the axial and rotational orientation of the screw 106.

When the appropriate lime is reached, the screw 106 may be repositioned by again inserting the driver into the through hole 104. This includes vertically aligning the driver with respect to the screw opening 192. After this alignment is complete, the driver is moved deeper into the through hole 104 so that the driver is received within the opening 192. Thereafter, the driver is rotated in a counterclockwise direction, which causes the screw 106 to rotate counterclockwise and discontinue the wedge fixing the axial and rotational orientation of the screw. Again, working backwards, counterclockwise rotation of the screw 106 causes the second washer 302 to be vertically repositioned along the screw head 180 so that the distance between the bottom surface 308 of the second washer and the top surface 142 of the first washer decreases.

At this point, the axial and/or rotational orientation of the screw 106 may be changed using the driver, followed by clockwise rotation of the screw to again form a wedge locking the screw in a second, different orientation. Alternatively, the screw 106 may be completely removed from the through hole 104, which would include counterclockwise rotation of the screw until its threads 190 no longer engage the threads 316 of the second washer 302, thereby allowing the screw to be removed from the through hole 104. Though not required, removal of the screw 106 from the through hole 104 may also include removal of one or both of the washers 140, 302 from the through hole.

Figure 22:
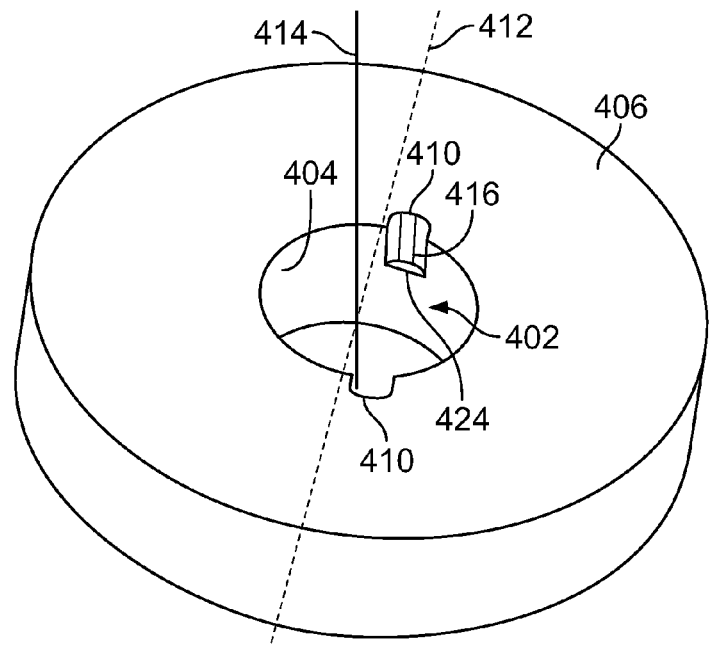
FIG. 22 is an elevated perspective view of an alternate plate material that may be used with the first and second exemplary variable angle locking screw assemblies of FIGS. 1 and 18.
Figure 23:
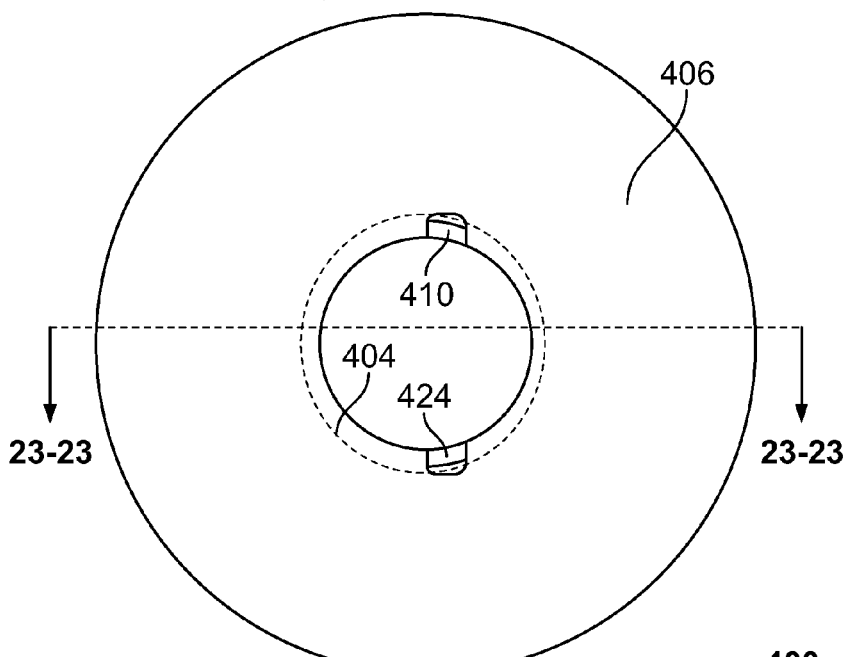
FIG. 23 is top view of the alternate plate material of FIG. 22.
Figure 24:
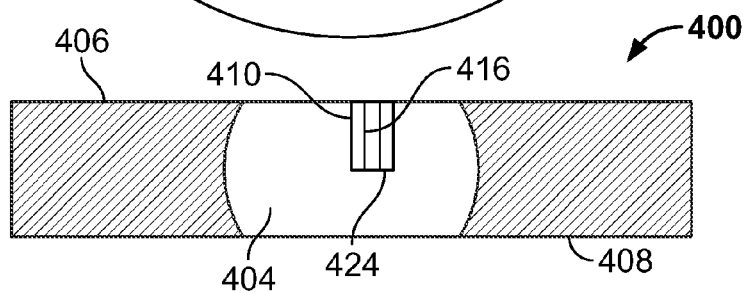
FIG. 24 is a cross-sectional view of the alternate plate material of FIG. 22 taken along line 22-23 of FIG. 23.

Referring to FIGS. 22-24, an alternate plate material 400 that may be used in addition to or in lieu of the first exemplary plate material 102 as part of each of the foregoing exemplary assemblies 100, 300. This alternate plate material 400 includes one or more through holes 402, with each through hole adapted to receive a screw 106 that concurrently mounts the plate material to bodily tissue such as, without limitation, bone (not shown). Because the plate material 400 may not always be planar, there are instances where the surgical screw should be oriented at an angle, with respect to the top surface (if the plate material, other than perpendicular.

A number of walls define the through holes 402 in the plate material 400. These walls include a spherical wall 404 that extends from a lop surface 406 spaced apart from a bottom surface 408 of the plate material 400. Inset with respect to the spherical wall 404 are opposed cutouts 410 that are offset on the same side of a horizontal diametric line 412 that extends through the axial center 414 of the through hole 402. Each cutout 410 is defined by a U-shaped side wall 416 that is substantially perpendicular to the top surface 406, where a portion of the U-shaped side wall lies along the diametric line 412. Each cutout 410 is also partially defined by a horizontal wall 424, located approximately at the middle of the through hole 402, which is substantially parallel to the top and bottom surfaces 406, 408. This horizontal wall 424 intersects the bottom of the U-shaped side wall 416 to create the cutout 410.

In exemplary form, the procedure for inserting or removing the washers 140, 160, 302 from the through hole 402 differs from that discussed with respect to the first exemplary plate material 102. By way of exemplary explanation, the first washer 140 may be inserted into the through hole 402 so that the washer is oriented vertically (i.e., on its side where the top and bottom surfaces 142, 144 are perpendicular to the horizontal plane), as opposed to horizontally. When lowered into the through hole 402 the top and bottom surfaces 142, 144 of the first washer are generally in parallel to and in between, the vertical side walls 416, 418 of the cutouts 410. As the first washer 140 is lowered into the through hole 402, the washer eventually is vertically centered within the through hole 402, but within the cutout 410. At this point, the washer 140 is laterally or horizontally repositioned to the other side of the diametric line 412, opposite the cutouts 410, so that the spherical wall 404 is operative to retain the washer within the through hole in a vertically oriented position. This repositioning of the first washer 140 clears the cutouts 410 to receive the second washer 160, 302. In like manner to the first washer 140, the second washer 160, 302 is lowered into the through hole 402 on its side so the top and bottom surfaces of the second washer are generally in parallel to, and in between, the vertical side walls 416, 418 of the cutouts 410. Eventually, the second washer 160, 302 is vertically centered within the through hole 402 and adjacent to the first washer 140. At this point, the first and second washers are turned approximately ninety degrees so that the second washer (either 160 or 302) sits above and on the first washer 140, with the spherical wall 404 being operative to retain the first washer within the through hole 402. Thus, after the washers are turned and the spherical wall 404 is operative to retain the washers therein, insertion of the screw 106 may occur as described above for the first and second exemplary embodiments 100, 300.

Similar to installing the washers 140, 160, 302 within the through hole 402, extraction occurs one at a time. More specifically, the washers 140, 160, 302 may be removed from the through hole 402 using a reverse process that is precisely the opposite of how the washers were inserted into the through hole.

Figure 25:
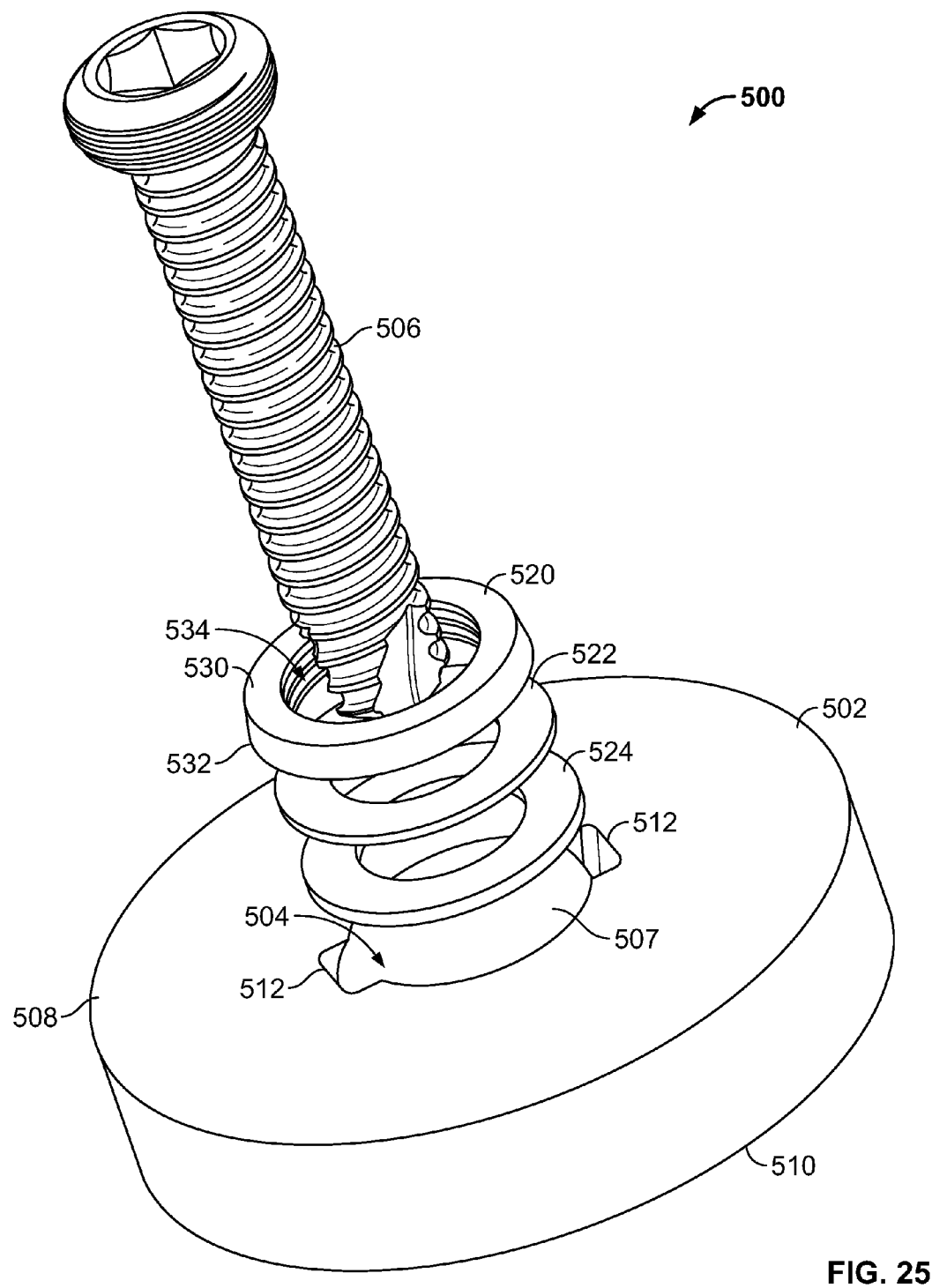
FIG. 25 is an exploded view of a third exemplary variable angle locking screw assembly.

Referring to FIG. 25, a second exemplary variable angle locking screw assembly 500 includes a plate material 502 having one or more through holes 504, with each through hole adapted to receive a screw 506 that concurrently mounts the plate material to bodily tissue such as, without limitation, bone (not shown). Because there are instances where the screw 506 is intended to be angled with respect to the plate material 502 other than perpendicular, it is advantageous to provide a mechanism that allows the screw to be oriented at angles and rotational positions other than perpendicular, while being secured to the plate material. At the same time, the angle of the screw 506 with respect to the plate material may not necessarily be predetermined, so providing flexibility as to the angular orientation of the screw may be advantageous.

Referring to FIGS. 25-30, a number of walls define the through holes 504 in the plate material 502. These walls include a semi-spherical wall 507 that defines the majority of the through hole 504 and is truncated at the top and bottom (i.e., poles). In this exemplary embodiment, the semi-spherical wall 507 has a maximum diameter at the midpoint between the top and bottom surfaces 508, 510 of the plate material 502. In other words, the minimum diameter of the through hole 504 is at the top and bottom surfaces 508, 510, but for two cutouts 512 formed into the semi-spherical wall 507. Each cutout 512 is formed opposite one another and extends from the top surface 508 vertically down until reaching a horizontal ledge 514 vertically located just below the approximate vertical midpoint of the semi-spherical wall 507. The width of each cutout 512, delineated by opposing walls 526, is dimensioned to slightly exceed the combined thicknesses (straight line distance between top to bottom surfaces) of the three washers 520, 522, 524 being adjacent one another. Similarly, the depth of each cutout 512 away from the axial center of the through hole 504, is delineated by a vertical wall 526 that bridges the opposing walls 526, where the distance between the opposing walls exceeds the aggregate thickness of the three washers 520, 522, 524.

Referencing FIGS. 25-30, the first washer 520 includes opposed top and bottom surfaces 530, 532 that are substantially planar and ring-shaped to outline a through hole 534. The through hole 534 is delineated by a circumferential interior surface having helical threads 536 that are adapted to engage the threads on the screw head. An outer circumferential surface 538 extends between the top and bottom surfaces 530, 532 and includes an arcuate or tapered shape. In this manner, the outside diameter at the bottom surface 532 exceeds the outside diameter at the top surface 530.

Referring to FIGS. 25-30, the second washer 522 is a Belleville washer or spring that includes opposed top and bottom surfaces 540, 542 having a hole 544 extending therethrough. An interior circumferential surface 546 is generally perpendicular with respect to the top and bottom surfaces 540, 542. Likewise, the second washer 522 includes an outer circumferential surface 548 that is radially spaced apart from the interior circumferential surface 546 and is generally perpendicular with respect to the lop and bottom surfaces 540, 542.

Referencing FIGS. 25-30, the third washer 524 includes opposed top and bottom surfaces 550, 552 that are substantially planar and circular to define a through hole 554. The through hole 554 is defined by a circumferential interior surface that extends between the lop and bottom surfaces 550, 552. The dimensions of the through hole 554 are such that the head of the screw cannot pass therethrough. An outer circumferential surface 558 extends between the top and bottom surfaces 550, 552 and includes an arcuate or tapered shape. In this manner, the outside diameter at the bottom surface 552 is less than the outside diameter at the top surface 550. Accordingly, the slope or arcuate nature of the outer circumferential surface 558 of the third washer 524 is generally the mirror image of the slope or arcuate nature of the outer circumferential surface 538 of the first washer 520.

Referring to FIGS. 25-30, the screw 506 includes a head 560 and an elongated shaft 562 that extends from the head. The head 560 is generally circular is horizontal cross-section and includes a substantially planar top surface 564 spaced apart from a conical bottom surface 566 that tapers and narrows in diameter as the distance from the top surface increases. A circumferential surface 568 of the head 560, which extends between the top and bottom surfaces 564, 566, is substantially smooth, but includes threads 570 that extend helically around the head. This circumferential surface 568 in combination with the threads 570 delineates the widthwise dimension of the screw head 560. An opening 572 extends from the top surface 564 normally into the interior of the head 506 and is bounded by six vertical walls 574 oriented in a hexagonal pattern that transition into a conically shaped floor 576. The conical floor 576 extends partially into the interior of the elongated shaft 562 that extends normally from the bottom surface 566 of the head 560. The elongated shaft 562 is generally cylindrical in shape and includes threads 578 helically distributed from proximate the bottom surface 566 of the head 560 to the conical tip (not shown) of the elongated shaft. It should be noted that the widthwise dimension of the head 560 is substantially larger than the widthwise dimension of the elongated shaft 562 so that the bottom surface 566 of the head that extends laterally outward (i.e., widthwise) beyond the elongated shaft and provides a conical plateau.

Figure 26:
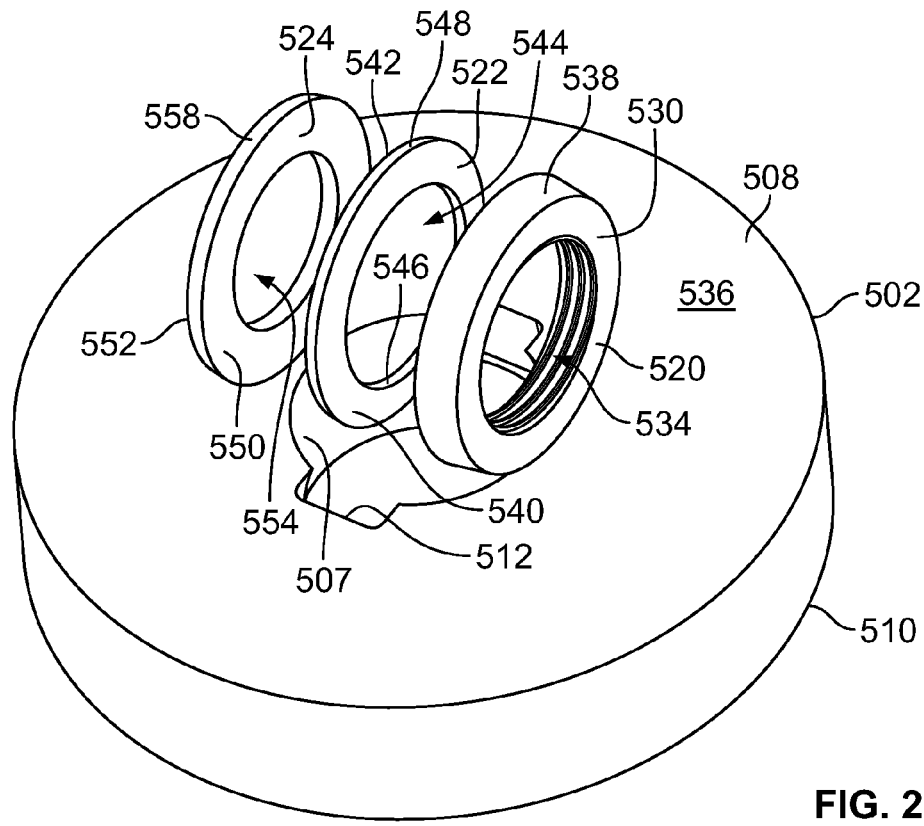
FIG. 26 is a partial exploded view of the washers and plate material of the third exemplary variable angle locking screw assembly of FIG. 25.
Figure 27:
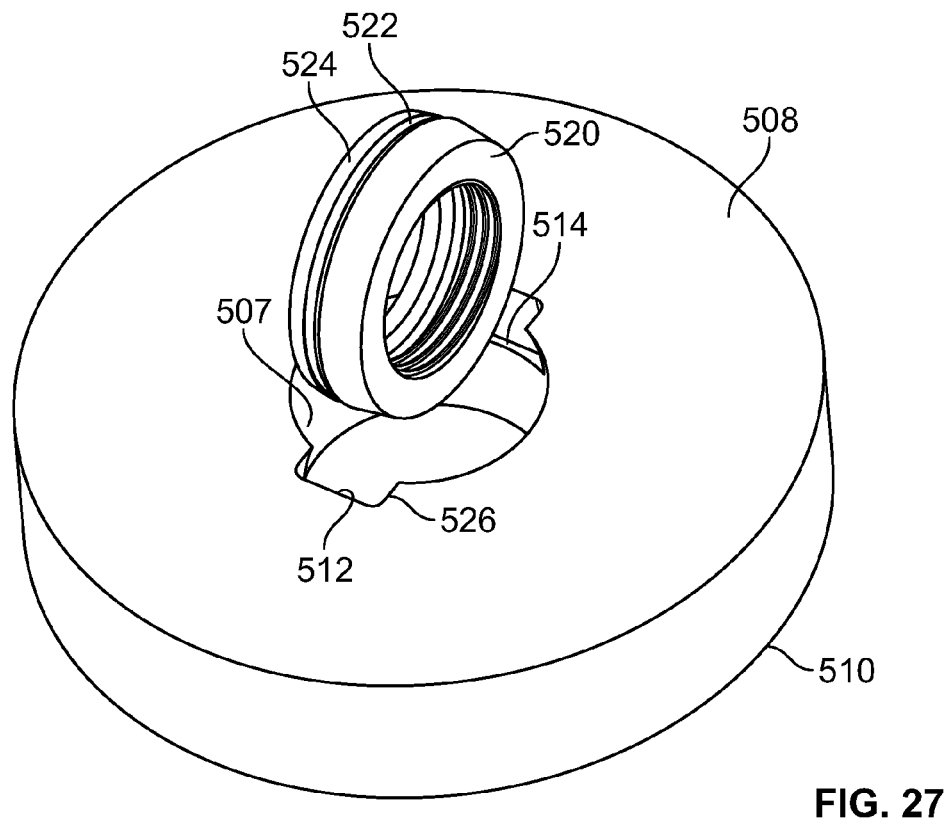
FIG. 27 is an elevated perspective view of the washers of the third exemplary variable angle locking screw assembly of FIG. 25 just prior to vertical insertion into the plate material.

Referencing FIGS. 26 and 27, fitting together the second exemplary variable angle locking screw assembly 500 includes correctly orienting the washers 520, 522, 524 with respect to one another. This includes orienting the first washer 520 so that its top surface 530 faces away from the other two washers 522, 524. The bottom surface 532 of the first washer 520 is oriented to face the top surface 540 of the second washer 522. And the bottom surface 542 of the second washer 522 is oriented to face the top surface 550 of the third washer 524. At the same time, the axial centers of the washer through holes 534, 544, 554 are aligned coaxially, while the washers are positioned adjacent one another as shown in FIG. 27.

Figure 28:
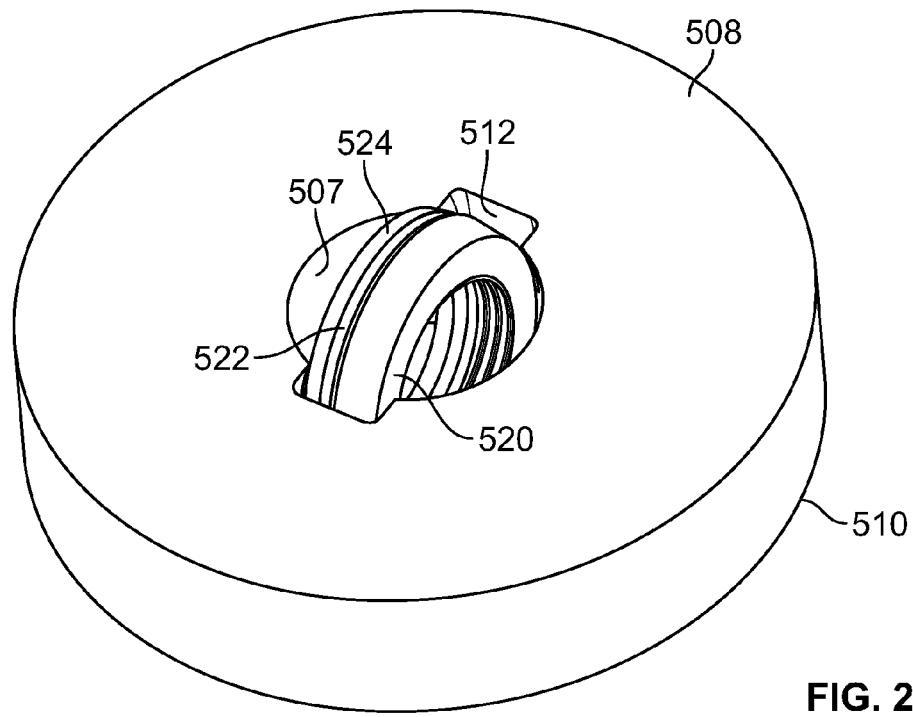
FIG. 28 an elevated perspective view of the washers of the third exemplary variable angle locking screw assembly of FIG. 25 subsequent to vertical insertion into the plate material.

Referring to FIGS. 27 and 28, the sandwiched washers 520, 522, 524 are then properly oriented with respect to the plate material 502. In exemplary fashion, the sandwiched washers 520, 522, 524 are oriented so that the axial center of the through holes 534, 544, 554 is perpendicular with respect to the axial center of the plate through hole 504. At the same time, the sandwiched washers 520, 522, 524 are centered laterally between opposing vertical walls 526 of the cutouts 512. Likewise, the sandwiched washers 520, 522, 524 are horizontally centered between opposing walls 526 of the cutouts 512. In this manner, the sandwiched washers 520, 522, 524 are lowered into the through hole 504 until the washers are vertically centered within the through hole. Generally, this position also coincides with the leading circumferential surfaces 538, 548, 558 of the washers 520, 522, 524 being seated upon the ledges 514. Upon reaching the ledges 514, the washers 520, 522, 524 while compressed are turned ninety degrees so that the axial center of the through holes 534, 544, 554 is parallel with respect to the axial center of the plate through hole 504, and so the top surface 530 of the first washer 520 faces in the same direction as the top surface 508 of the plate material 502 (sec an approximate position in FIG. 29). Because the external diameter (i.e., horizontal width) of the third washer 524 is greater than the diameter of the plate through hole 504 at the bottom surface 510, the washers are retained within the through hole. Specifically, the outer circumferential surface 558 of the third washer rests against the spherical wall 507, which prohibits the washers 520, 522, 524 from passing completely through the hole 504. At the same time, the through hole 504 and washers 520, 522, 524 are sized so that when the washers are located within the hole by themselves, the second washer 522 acts as a spring to push upward on the bottom surface 532 of the first washer 522 and downward on the top surface 550 of the third washer 524. This spring force causes the outer circumferential surfaces 538, 558 of both washers 520, 524 to generally retard, through sufficient friction, circular motion (i.e., clockwise or counterclockwise) of the washers 520, 524 with respect to the spherical wall 507.

Figure 29:
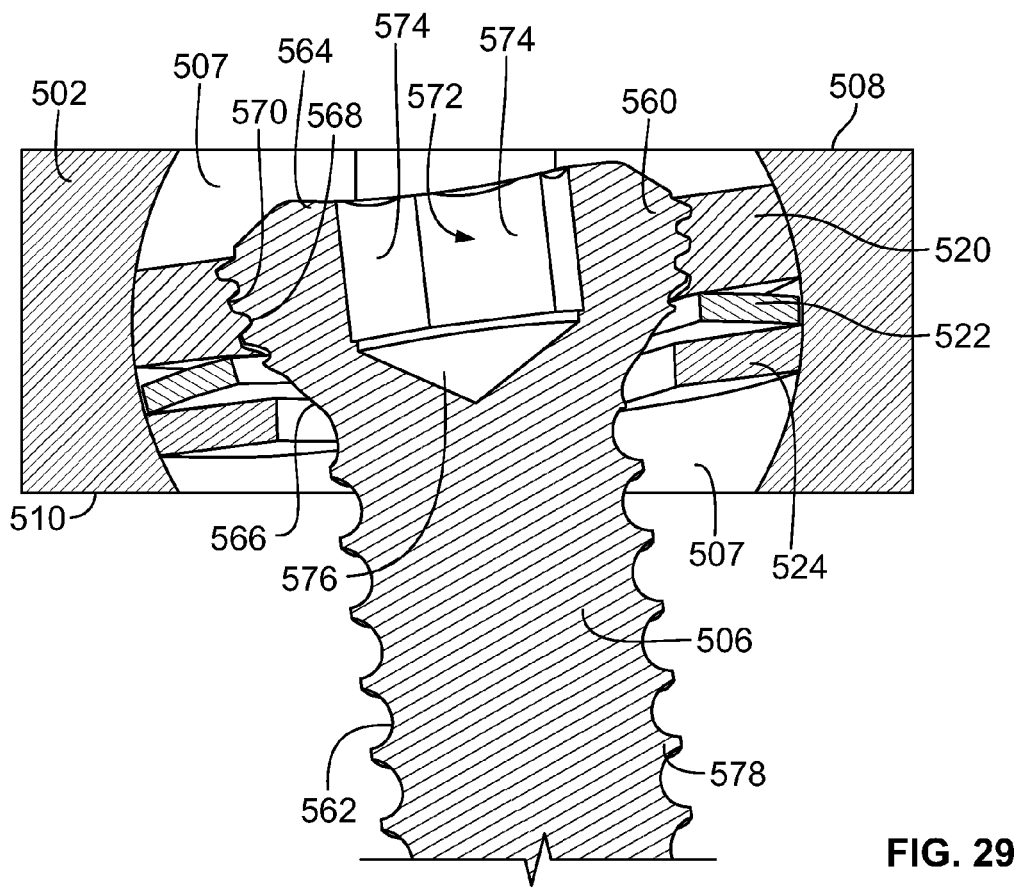
FIG. 29 is a cross-sectional view of the plate material, washers, and screw of the third exemplary variable angle locking screw assembly of FIG. 25, prior to locking of the screw in a fixed orientation.
Figure 30:
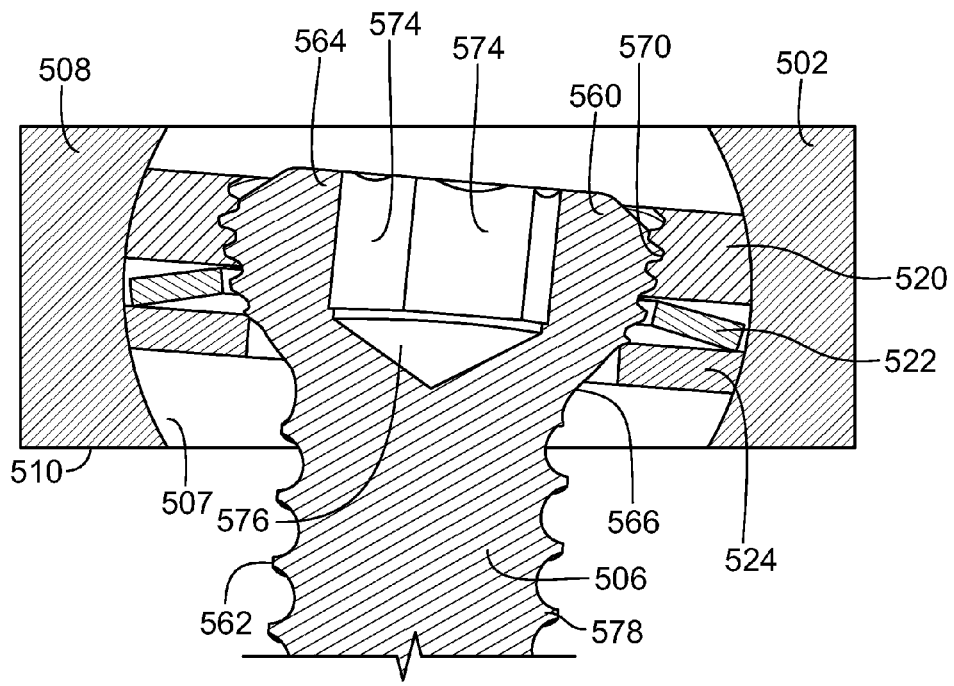
FIG. 30 is a cross-sectional view of the plate material, washers, and screw used with the third exemplary variable angle locking screw assembly of FIG. 25, subsequent to locking of the screw in a fixed orientation.
Figure 31:
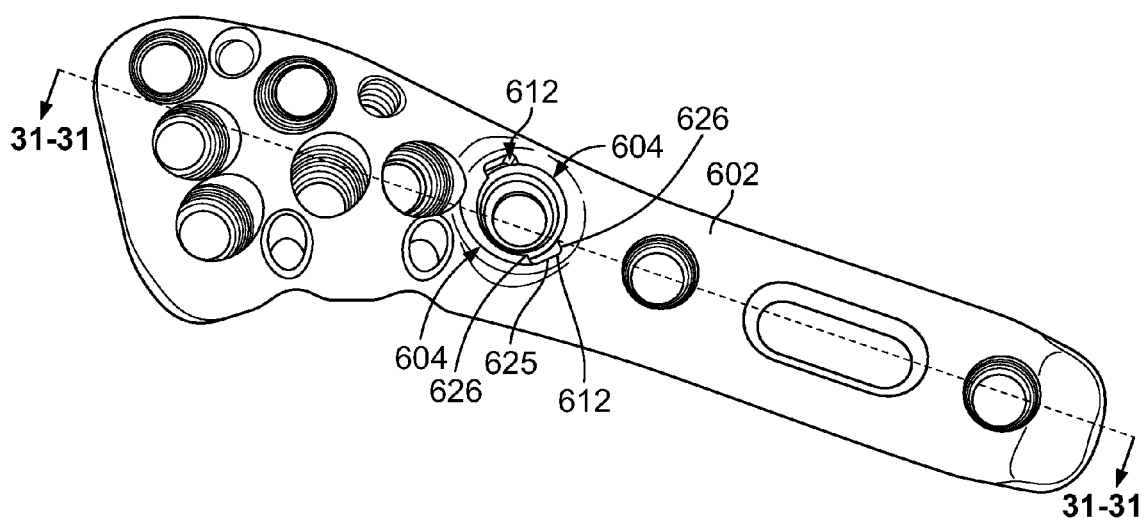
FIG. 31 is an elevated perspective view of a third exemplary variable angle locking screw assembly.
Figure 32:
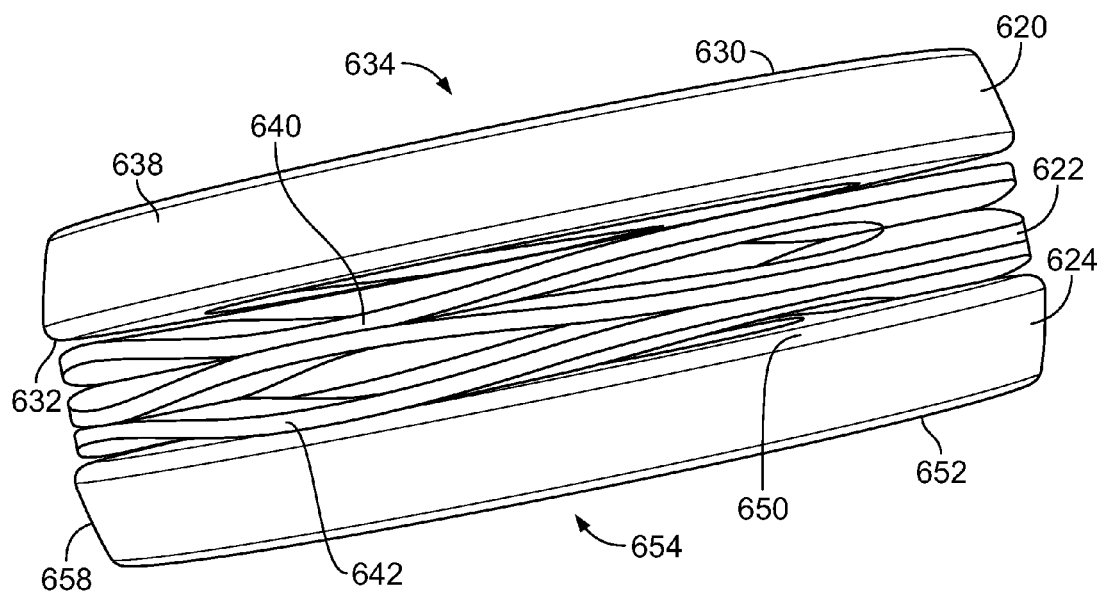
FIG. 32 is a profile view of three washers comprising part of the third exemplary variable angle locking screw assembly of FIG. 31.
Figure 33:
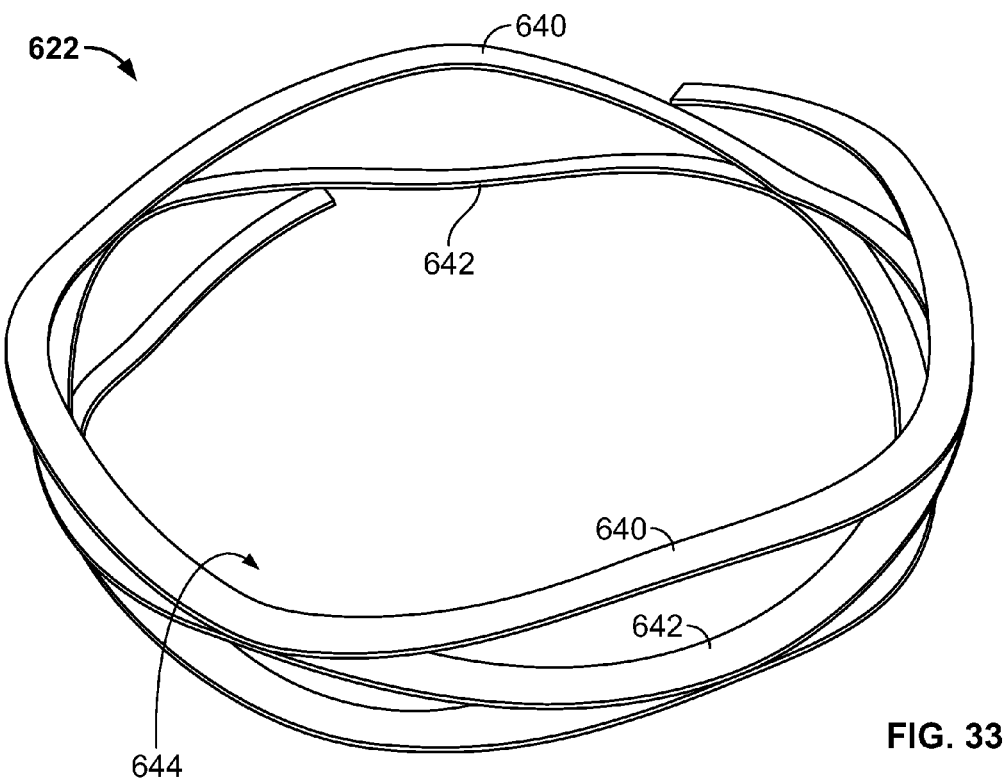
FIG. 33 is an elevated perspective of an exemplary wave spring washer comprising part of the third exemplary variable angle locking screw assembly of FIG. 31.

Referring to FIGS. 29 and 30, the tip of the screw 506 is inserted first into the through hole 504 in the plate material 502 and aligned to extend through the holes 534, 544, 554 in the washers 520, 522, 524. The tip 580 and shaft 562 is then inserted into the through hole 504 in the plate material 502 and into the holes 534, 544, 554 in the washers 520, 522, 524 until the tip passes completely therethrough. At this point, the shaft 562 of the screw also extends through the holes 504, 534, 544, 554, with the head 560 being on the opposite side of the plate material 502 as is the tip. Continued movement of the screw further into the hole 504 in the plate material 502 finally reaches a point where the head 560 enters the hole 504 and its threads 570 reach and engage the threads 536 the first washer 520. At this point, vertical motion of the head 560 further into the hole 504 requires rotation of the head with respect to the first washer 520. And it is at this lime that the angular and rotational orientation of the screw 506 with respect to the plate material 502 may be established.

As discussed above, the second washer 522 provides a sufficient spring force to cause the outer circumferential surfaces 538, 558 of both washers 520, 524 to contact the spherical wall 507 and generally retard, through sufficient friction, circular motion of the washers 520, 524 with respect to plate material 502. But this frictional force is not sufficient to inhibit angular adjustment of the screw 506 and, consequently, angular adjustment of the washers 534, 544, 554. As such, the screw 506 and washers 534, 544, 554 may be axially adjusted in all 360 degrees approximate an axial deflection from perpendicular (extending along the vertical axis of the through hole 504) to about thirty degrees. Accordingly, at any time prior to the screw 506 being locked in position, as will be discussed below, it may be possible to change the angular and rotational orientation of the screw (presuming the screw-bone interface allows such a change).

Rotation of the head 560 while the first washer 520 remains stationary (or with minimal circular motion with respect to the plate material 502) causes the threads 536, 570 to engage one another and draw the head into the hole 534. Eventually, continued rotation of the head 560 draws the head far enough into the hole 534 so that the bottom surface 566 contacts the third washer 524. Specifically, the diameter of the through hole 554 of the third washer 524 is smaller than the largest diameter of the bottom surface 566 of the head 560 so that through put of the head beyond the third washer is impossible. In this manner, the top surface 550 of the third washer 524 provides a circumferential flange upon which the bottom surface 566 of the screw head 560 is seated after the screw head reaches a predetermined depth within the through hole 504. After the bottom surface 566 of the head 560 reaches the top surface 550 of the third washer 524 (see FIG. 30), continued rotation of the screw is operative to drive the first washer 520 vertically away from the third washer.

The maximum vertical distance between the first and third washers 520, 524 is a function of the shape/dimensions of the washers, the shape/dimensions of the through hole 504. In this exemplary embodiment, the first and third washers 520, 524 are sized and shaped so that the maximum distance between the two washers while within the through hole 504 is not greater than the distance between the top and bottom surfaces 564, 566 of the screw head 560. At the same lime, the size and shape of the spherical wall 507 compliments the shape and size of the washers 520, 524 so that the before reaching the maximum spacing between the washers, the washers cooperate with the screw head 560 to form a wedge against the semi-spherical wall 507 that locks the angular and rotational position of the screw 506.

In this exemplary embodiment, the washers 520, 524 and screw head 560 cooperate to create a press or wedge that exerts sufficient pressure against the semi-spherical wall 507 to fix the rotational and angular orientation of the screw 506 and the washers 520, 522, 524 with respect to the plate material 502. In order to accomplish this, the diameter of the through hole 554 of the third washer 524 is smaller than the diameter of the bottom surface 566 of the head 560. This means that no matter how much the screw 506 is rotated or repositioned vertically within the through hole 554, the third washer 524 provides a stop that retards the screw head 560 from going beyond the third washer. But the same is not true for the interaction between the first washer 520 and the screw 506. As discussed above, the threads 536, 570 of the screw head 560 and the first washer 520 are sized to engage one another so that rotational motion of the screw with respect to the first washer, while the threads are engaged, causes a shift in the vertical position of the screw with respect to the first washer. In exemplary form, the threads 536, 570 of the screw head 560 and the first washer 520 interact to cause the screw to be vertically lowered with respect to the first washer when the screw is rotated in a clockwise direction. Conversely, the threads 536, 570 of the screw head 560 and the first washer 520 interact to cause the screw to be vertically raised with respect to the first washer when the screw is rotated in a counterclockwise direction. As a result, when the screw 506 is inserted into the through hole 506 and repositioned so that the bottom surface 566 of the head 560 contacts the third washer 524, rotation of the screw operates to change the vertical position of the first washer 520 with respect to the screw head and third washer 524.

Referring back to FIG. 29, the screw head 560 has been rotated with respect to the first washer 520 while the second washer 522 exerts a spring force against the first and third washers 520, 524 so that rotation of the first washer does not substantially occur when the screw head is rotated. Engagement of the threads 536, 570 while the screw 506 is rotated (for example, in this case, clockwise) causes the first washer 520 to vertically travel along the screw head 560 and away from the third washer 524. Eventually, as the screw 506 is rotated to vertically reposition the first washer 520 and the spacing between the washers 520, 524 reaches a predetermined point, the force required to rotate the screw drastically increases.

Referencing FIG. 30, the dimensions of the spherical wall 507 set the outer bounds of maximum vertical expansion between the washers 520, 524. As a result, when the washers 520, 524 reach the point of maximum expansion, the torque exerted on the screw is insufficient to overcome the forces acting on the washers by the plate 502. At this moment, the torque exerted on the screw 506 operates to create a first mechanical lock between the threads 536, 570 and a second mechanical lock between the washers 520, 524 and the spherical wall 507. The first and second mechanical locks work in tandem to secure the rotational and angular orientation of the screw 506. These mechanical locks may be disengaged simply by rotating the screw 506 in the opposite direction (for example, in this case, counterclockwise), which causes the washers 520, 524 to initially move closer together so that rotational and angular adjustment of the screw is possible (presuming the screw-to-bone interface allows such an adjustment).

The foregoing components of the second exemplary variable angle locking screw assembly 500 may be fabricated from any biologically stable material. By way of example, and not limitation, the plate material 502 may be fabricated from titanium, while the washers 520, 522, 524 may be fabricated from stainless steel, while the screw 506 may be fabricated from tungsten.

While the second exemplary variable angle kicking screw assembly 500 has been described with the washer 522 comprising a Belleville washer, it is also within the scope of use other springs such as helical coils and discontinuous helical washers.

Referring to FIGS. 31-36, a third exemplary variable angle locking screw assembly 600 includes a plate material 602 having one or more through holes 604, with at least one of the through holes adapted to receive a screw 606 that concurrently mounts the plate material to bodily tissue such as, without limitation, bone (not shown). Because there are instances where the screw 606 is intended to be angled with respect to the plate material 602 other than perpendicular, it is advantageous to provide a mechanism that allows the screw to be oriented at angles and rotational positions other than perpendicular, while being secured to the plate material. At the same time, the angle of the screw 606 with respect to the plate material may not necessarily be predetermined, so providing flexibility as to the angular orientation of the screw may be advantageous.

Referring to FIGS. 31 and 34-36, a number of walls define the through hole 604 in the plate material 602. These walls include a semi-spherical wall 607 that defines the majority of the through hole 604 and is truncated at the top and bottom (i.e., poles). In this exemplary embodiment, the semi-spherical wall 607 has a maximum diameter at the midpoint between the top and bottom surfaces 608, 610 of the plate material 602. In other words, the minimum diameter of the semi-spherical wall 607 defining the through hole 604 is at the top and bottom surfaces 608, 610, but for two cutouts 612 formed into the semi-spherical wall 607. Each cutout 612 is formed opposite one another and extends from the top surface 608 vertically down until reaching a horizontal ledge 614 vertically located just below the approximate vertical midpoint, of the semi-spherical wall 607. The width of each cutout 612, delineated by opposing walls 626, is dimensioned to slightly exceed the combined thicknesses (straight line distance between top to bottom surfaces) of the three washers 620, 622, 624 being adjacent one another. Similarly, the depth of each cutout 612 away from the axial center of the through hole 604, is delineated by a vertical wall 625 that bridges the opposing walls 626.

Referencing FIGS. 32 and 34-36, the first washer 620 includes opposed top and bottom surfaces 630, 632 that are substantially planar and ring-shaped to outline a through hole 534. The through hole 634 is delineated by a circumferential interior surface having helical threads 636 that are adapted to engage the threads on the screw head. An outer circumferential surface 638 extends between the top and bottom surfaces 630, 632 and includes an arcuate or tapered shape. In this manner, the outside diameter at the bottom surface 632 exceeds the outside diameter at the top surface 630.

Referring to FIGS. 32-36, the second washer 622 is a wave spring washer fabricated from a single helical strand. The helical strand is fabricated from metal and includes alternating, circumferential crests 640 and troughs 642 in order to provide a profile wave pattern. The wave pattern is structured so that the radial highest point of each crest is aligned and contacts the radial lowest point of an adjacent layer trough. In this manner, only select points of each strand layer contact one another in order to provide a spring force. By way of example, the second washer 622 includes three layers or windings. However, it should be noted that greater or fewer than three windings may be used to construct the second washer 622. The helical strand of the second washer 622 defines a circular through hole 644 and is dimensioned to have a mean diameter approximating the diameter of the first washer 620 bottom and the third washer 624 top.

Referencing FIGS. 32 and 34-36, the third washer 624 includes opposed top and bottom surfaces 650, 652 that are substantially planar and circular to define a through hole 654. The through hole 654 is defined by a circumferential interior surface that extends between the top and bottom surfaces 650, 652. The dimensions of the through hole 654 inhibit the head of the screw to pass therethrough. An outer circumferential surface 658 extends between the top and bottom surfaces 650, 652 and includes an arcuate or tapered shape. In this manner, the outer diameter at the bottom surface 652 is less than the outer diameter at the top surface 650. Accordingly, the slope or arcuate nature of the outer circumferential surface 658 of the third washer 624 is generally the mirror image of the slope or arcuate nature of the outer circumferential surface 638 of the first washer 620.

Figure 36:
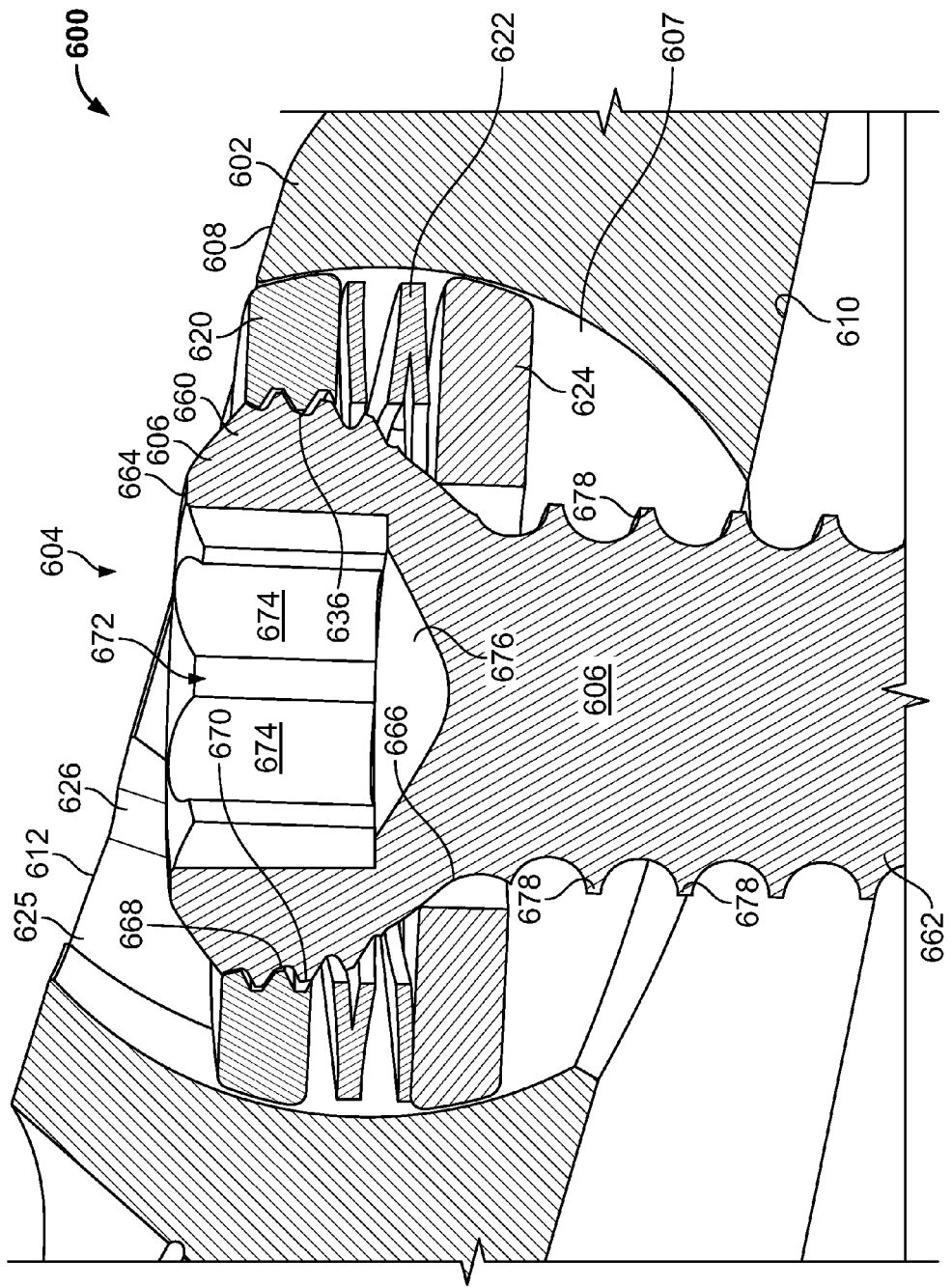
FIG. 36 is a cross-sectional view of the third exemplary variable angle locking screw assembly taken along line 31-31 of FIG. 31, shown with the locking screw being inserted and oriented in a locked position.

Referring to FIG. 36, the screw 606 is very similar to the screws discussed in the foregoing exemplary embodiments. In this exemplary embodiment, the screw 606 includes a head 660 and an elongated shall 662 that extends from the head. The head 660 is generally circular is horizontal cross-section and includes a substantially planar top surface 664 spaced apart from a conical bottom surface (not shown) that tapers and narrows in diameter as the distance from the top surface increases. A circumferential surface 668 of the head 660, which extends between the top and bottom surfaces 664, 666, includes threads 670 that extend helically around the head. This circumferential surface 668 in combination with the threads 670 delineates the widthwise dimension of the screw head 660. An opening, 672 extends from the top surface 664 normally into the interior of the head 660 and is bounded by vertical walls 674 that transition into a conically shaped floor 676. The conical floor 676 extends partially into the interior of the elongated shaft 662. The elongated shaft 662 is generally cylindrical in shape and includes threads 678 helically distributed from proximate the bottom surface 666 of the head 660 to the conical tip (not shown) of the elongated shaft. It should be noted that the widthwise dimension of the head 660 is substantially larger than the widthwise dimension of the elongated shah 662 so that the bottom surface 666 of the head forms a conical plateau.

Figure 34:
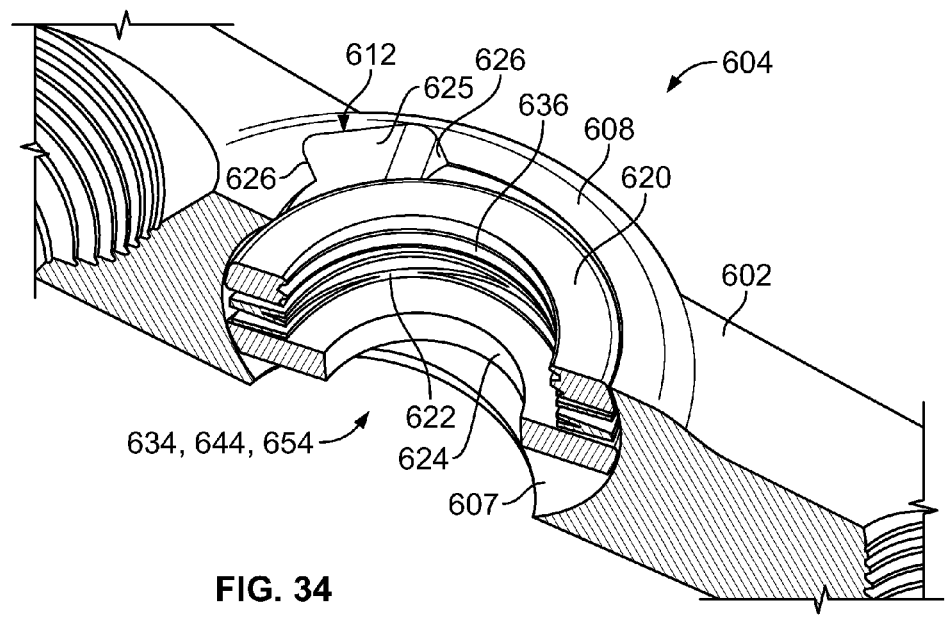
FIG. 34 is an elevated perspective, cross-sectional view of the third exemplary-variable angle locking screw assembly taken along line 31-31 of FIG. 31.
Figure 35:
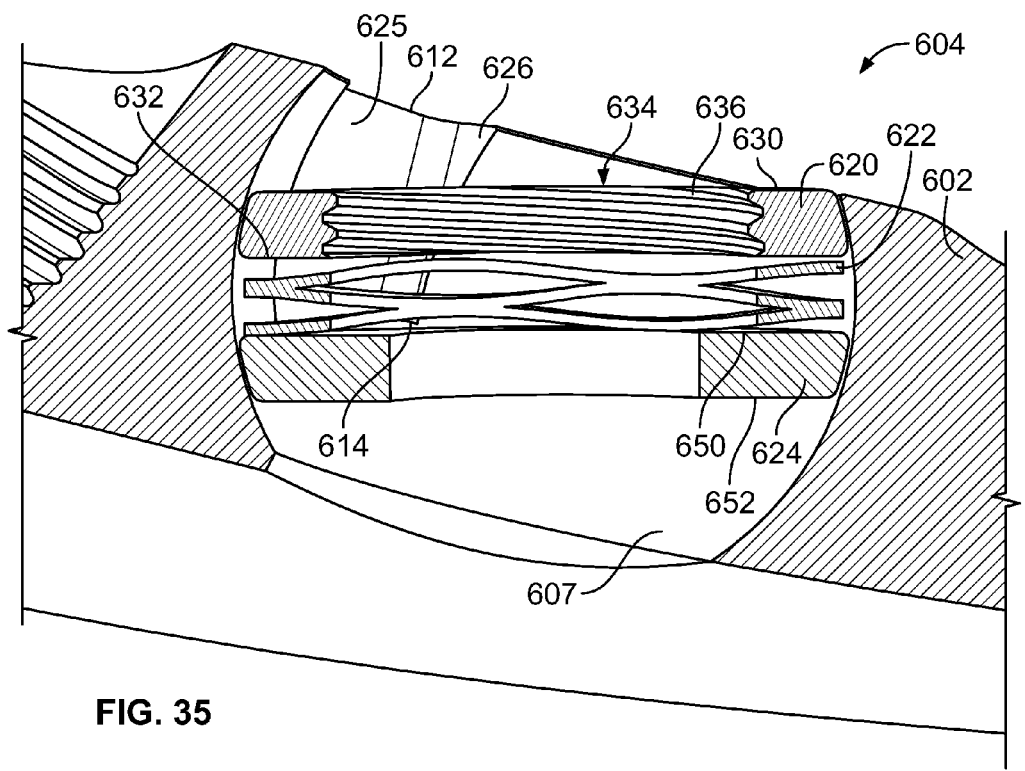
FIG. 35 is a cross-sectional view of the third exemplary variable angle locking screw assembly taken along line 31-31 of FIG. 31.

Referencing FIGS. 34-36, fitting together the components of the third exemplary variable angle locking screw assembly 600 includes correctly orienting the washers 620, 622, 624 with respect to one another. This includes orienting the first washer 620 so that its top surface 630 faces away from the other two washers 622, 624. The bottom surface 632 of the first washer 620 is oriented to contact of the second washer 622 so the washers are generally axially aligned. And the third washer 624 is also axially aligned with the other two washers 620, 622 and positioned so that the bottom surface 652 faces away from the first and second washers. This is referred to as the sandwich position (see FIG. 32).

The sandwiched washers 620, 622, 624 are then properly oriented with respect to the plate material 602. In exemplary fashion, the sandwiched washers 620, 622, 624 are oriented so that the axial center of the through holes 634, 644, 654 is perpendicular with respect to the axial center of the plate through hole 604. At the same time, the sandwiched washers 620, 622, 624 are centered laterally between opposing vertical walls 526 of the cutouts 612. Likewise, the sandwiched washers 620, 622, 624 are horizontally centered between opposing walls 626 of the cutouts 612. In this manner, the sandwiched washers 620, 622, 624 are lowered into the through hole 604 until the washers are vertically centered within the through hole. Generally, this position also coincides with the leading circumferential surfaces 638, 658 of the washers 620, 624 being seated upon the ledges 614. Upon reaching the ledges 614, the washers 620, 622, 624 while compressed are turned ninety degrees so that the axial center of the through holes 634, 644, 654 is generally parallel with respect to the axial center of the plate through hole 604, and so the top surface 610 of the first washer 620 faces in generally the same direction as the top surface 608 of the plate material 602 (see an approximate position in FIG. 34). Because the external diameter (i.e., horizontal width) of the third washer 624 is greater than the diameter of the plate through hole 604 at the bottom surface 610, the washers are retained within the through hole. Specifically, the outer circumferential surface 658 of the third washer rests against the spherical wall 607, which prohibits the washers 620, 622, 624 from passing completely through the hole 604. At the same time, the through hole 604 and washers 620, 622, 624 are sized so that when the washers are located within the hole by themselves, the second washer 622 acts as a spring to push upward on the bottom surface 632 of the first washer 620 and downward on the top surface 650 of the third washer 624. This spring force causes the outer circumferential surfaces 638, 658 of both washers 620, 624 to generally retard, through sufficient friction, circular motion (i.e., clockwise or counterclockwise) of the washers 620, 624 with respect to the spherical wall 607.

After the washers 620, 622, 624 have been positioned and retained in the through hole 604, the tip of the screw 606 is inserted first into the through hole 604 in the plate material 602 and aligned to extend through the holes 634, 644, 654 in the washers 620, 622, 624. The tip and shaft 662 of the screw 606 is then inserted into the through hole 604 in the plate material 602 and through the holes 634, 644, 654 in the washers 620, 622, 624 until the tip passes completely therethrough. At this point, the shaft 662 of the screw 606 extends through the holes 604, 634, 644, 654, with the head 660 being on the opposite side of the plate material 602 as is the tip. Continued movement of the screw further into the hole 604 in the plate material 602 finally reaches a point where the threads 670 reach and engage the threads 636 the first washer 620. At this point, vertical motion of the head 660 further into the hole 604 requires rotation of the head with respect to the first washer 620. And it is at this time that the angular and rotational orientation of the screw 606 with respect to the plate material 602 may be fixed.

As discussed above, the second washer 622 provides a sufficient spring force to cause the outer circumferential surfaces 638, 658 of both washers 620, 624 to contact the spherical wall 607 and generally retard, through sufficient friction, circular motion of the washers 620, 624 with respect to plate material 602. But this frictional force is not sufficient to inhibit angular adjustment of the screw 606 and, consequently, angular adjustment of the washers 620, 622, 624. As such, the screw 606 and washers 620, 622, 624 may be axially adjusted in all 360 degrees approximate an axial angular deflection from perpendicular (extending along the vertical axis of the through hole 604) to about thirty degrees. Accordingly, at any time prior to the screw 606 being locked in position, as will be discussed below, it may be possible to change the angular and rotational orientation of the screw (presuming the screw-bone interface allows such a change).

Rotation of the head 660 while the first washer 620 remains stationary (or with minimal circular motion with respect to the plate material 602) causes the threads 636, 670 to engage one another and draw the head further into the hole 634. Eventually, continued rotation of the head 660 draws the head far enough into the hole 634 so that the bottom surface 666 contacts the third washer 624. Specifically, the diameter of the through hole 654 of the third washer 624 is smaller than the largest diameter of the bottom surface 666 of the head 660 so that throughput of the head beyond the third washer is impossible. In this manner, the top surface 650 of the third washer 624 provides a circumferential flange upon which the bottom surface 666 of the screw head 660 is seated after the screw head reaches a predetermined depth within the through hole 604. After the bottom surface 666 of the head 660 reaches the top surface 650 of the third washer 624 (see FIG. 36), continued rotation of the screw is operative to drive the first washer 620 vertically away from the third washer.

The maximum vertical distance between the first and third washers 620, 624 is a function of the shape/dimensions of the washers, the shape/dimensions of the through hole 604. In this exemplary embodiment, the first and third washers 620, 624 are sized and shaped so that the maximum distance between the two washers while within the through hole 604 is not greater than the distance between the top and bottom surfaces 664, 666 of the screw head 660. At the same time, the size and shape of the spherical wall 607 compliments the shape and size of the washers 620, 624 so that the before reaching the maximum spacing between the washers, the washers cooperate with the screw head 660 to form a wedge against the semi-spherical wall 607 that locks the angular and rotational position of the screw 606.

In this exemplary embodiment, the washers 620, 624 and screw head 660 cooperate to create a press or wedge that exerts sufficient pressure against the semi-spherical wall 607 to fix the rotational and angular orientation of the screw 606 and the washers 620, 622, 624 with respect to the plate material 602. In order to accomplish this, the diameter of the through hole 654 of the third washer 624 is smaller than the diameter of the bottom surface 666 of the head 660. This means that no matter how much the screw 606 is rotated or repositioned vertically within the through hole 654, the third washer 624 provides a stop that retards the screw head 660 from going beyond the third washer. But the same is not true for the interaction between the first washer 620 and the screw 606.

As discussed above, the threads 636, 670 of the screw head 660 and the first washer 620 are sized to engage one another so that rotational motion of the screw with respect to the first washer, while the threads are engaged, causes a shift in the vertical position of the screw with respect to the first washer. In exemplary form, the threads 636, 670 of the screw head 660 and the first washer 620 interact to cause the screw to be vertically lowered with respect to the first washer when the screw is rotated in a clockwise direction. Conversely, the threads 636, 670 of the screw head 660 and the first washer 620 interact to cause the screw to be vertically raised with respect to the first washer when the screw is rotated in a counterclockwise direction. As a result, when the screw 606 is inserted into the through hole 606 and repositioned so that the bottom surface 666 of the head 660 contacts the third washer 624, rotation of the screw operates to change the vertical position of the first washer 620 with respect to the screw head and third washer 624.

Referring back to FIG. 36, the screw head 660 has been rotated with respect to the first washer 620 while the second washer 622 exerts a spring force against the first and third washers 620, 624 so that rotation of the first washer does not substantially occur when the screw head is rotated. Engagement of the threads 636, 670 while the screw 606 is rotated (for example, in this case, clockwise) causes the first washer 620 to vertically travel along the screw head 660 and away from the third washer 624. Eventually, as the screw 606 is rotated to vertically reposition the first washer 620 so the vertical spacing between the washers 620, 624 reaches a predetermined point, the force required to rotate the screw drastically increases.

The dimensions of the spherical wail 607 set the outer bounds of maximum vertical expansion between the washers 620, 624. As a result, when the washers 620, 624 reach the point of maximum expansion, the torque exerted on the screw 606 is insufficient to overcome the forces acting on the washers by the plate 602. At this moment, the torque exerted on the screw 606 operates to create a first mechanical lock between the threads 636, 670 and a second mechanical lock between the washers 620, 624 and the spherical wall 607. The first and second mechanical locks work in tandem to secure the rotational and angular orientation of the screw 606. These mechanical locks may be disengaged simply by rotating the screw 606 in the opposite direction (for example, in this case, counterclockwise), which causes the washers 620, 624 to initially move closer together so that rotational and angular adjustment of the screw is possible (presuming the screw-to-bone interface allows such an adjustment).

The foregoing components of the third exemplary variable angle locking screw assembly 600 may be fabricated from any biologically stable material. By way of example, and not limitation, the plate material 602 may be fabricated from titanium, while the washers 620, 622, 624 may be fabricated from stainless steel, while the screw 606 may be fabricated from tungsten.

While the third exemplary variable angle locking screw assembly 600 has been described with the washer 622 comprising a wave spring washer, it is also within the scope of use other springs such as helical coils and discontinuous helical washers.

Referencing FIGS. 37-40, a fourth exemplary variable angle locking screw assembly 700 includes a pair of washers 702, 703 adapted to be received within a through hole 704 of a bone plate 706. In this exemplary embodiment, the bone plate 706 includes at least one through hole 704 extending from the top surface 708 to the bottom surface 710 of the plate. The through hole 704 is at least partially defined by a smooth spherical sidewall 712 operative to change the cross-sectional area of the hole along the vertical length of the hole. Consistent with a spherical sidewall 712, the horizontal cross-sections of the holes are generally circular with varying diameters. Specifically, the diameter of the through hole 704 at the top and bottom surfaces 708, 710, as defined by the spherical sidewalks 712, is at a minimum. In contrast, the maximum diameter of the through hole 704, as defined by the spherical sidewalks 712, is at the vertical midpoint of the hole that generally corresponds to the diameter of a sphere that would fit snuggly within the bounds of the hole.

Figure 38:
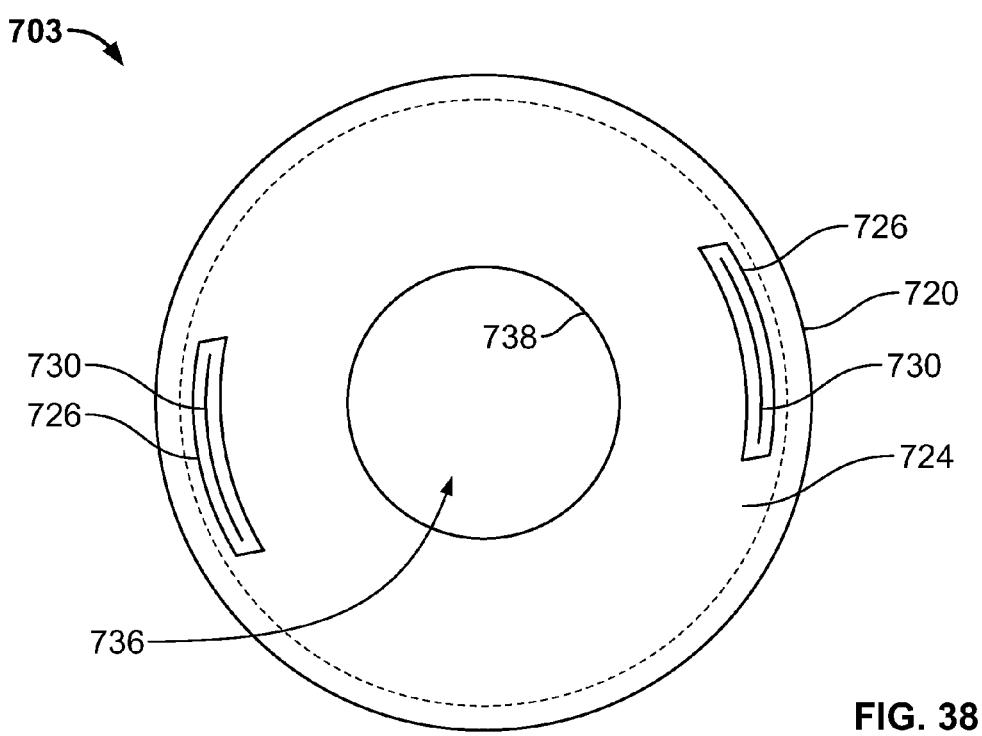
FIG. 38 is a top view of one washer comprising part of a fourth exemplary variable angle locking screw assembly.

Referring specifically to FIG. 38, a first of the washers 703 includes an arcuate, outer smooth circumferential surface 720 that extends between top and bottom surfaces 722, 724 of the washer. In this exemplary embodiment, the top and bottom surfaces 722, 724 are generally smooth and planar, with the exception of the bottom surface 722 that includes biased prongs 726 extending therefrom. Each biased prong 726 includes a curved vertical profile that generally tracks that of the outer circumferential surface 720. Each prong 726 is inset with respect to the outer circumferential surface and exhibits a sufficient curvature and vertical distance to engage a corresponding surface on the second washer 703.

In this exemplary embodiment, the prongs 726 are fabricated from the same metal as the remainder of the washer 703. In exemplary from, the height of the prongs 726 is at least as thick as the washer 703. But it should also be understood that taller and shorter prongs may be incorporated as part of the first washer 703. The lateral thickness of the prongs 726 is sufficient to inhibit fracture from the washer body, while at the same time not being so thick as to significantly retard deformation of the prongs that would lake away from their biased nature. Nearest the bottom surface 724, the prongs 726 have a slightly curved, rectangular base. This slightly curved, rectangular profile tapers as the distance from the bottom surface 724 increases, so that the far end of the prong exhibits an edge 730.

Figure 39:
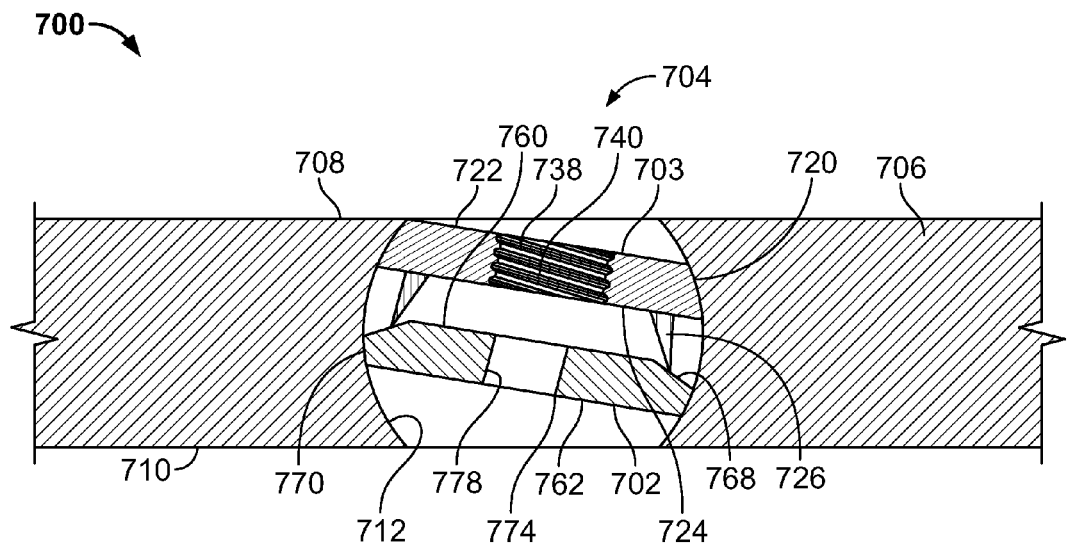
FIG. 39 is a cross-sectional view of the fourth exemplary variable angle locking screw assembly, without a locking screw, shown in the locked position.
Figure 40:
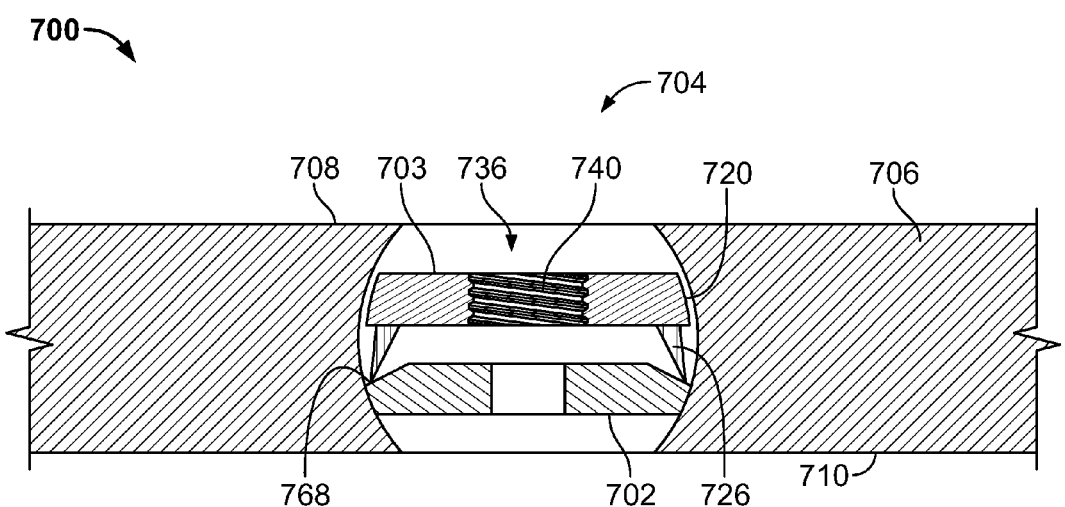
FIG. 40 is a cross-sectional view of the fourth exemplary variable angle locking screw assembly, without a locking screw, shown in the unlocked position.

As can be seen in FIGS. 39 and 40, the top and bottom surfaces 722, 724 of the first washer 703 are generally parallel to one another so that the vertical thickness between the surfaces is generally uniform. Both surfaces 722, 724 include a circumferential edge that intersects the circumferential surface 720. Likewise, both surfaces 722, 724 include an internal, centered circular edge that defines the top and bottom cross-section of a through opening 736 that extends between both surfaces. An internal wall 738 that defines the vertical, lengthwise dimensions of the opening 736 is circular in cross section and oriented generally perpendicular to the top and bottom surfaces 722, 724. In this manner, the through opening 736 includes a generally cylindrical shape hut for helical threads 740 that extend from the internal wall 738. These helical threads 740 are adapted to interface with threads on the head of a variable angle locking screw (not shown). And the prongs 726 are adapted to interface with the second washer 702.

Figure 37:
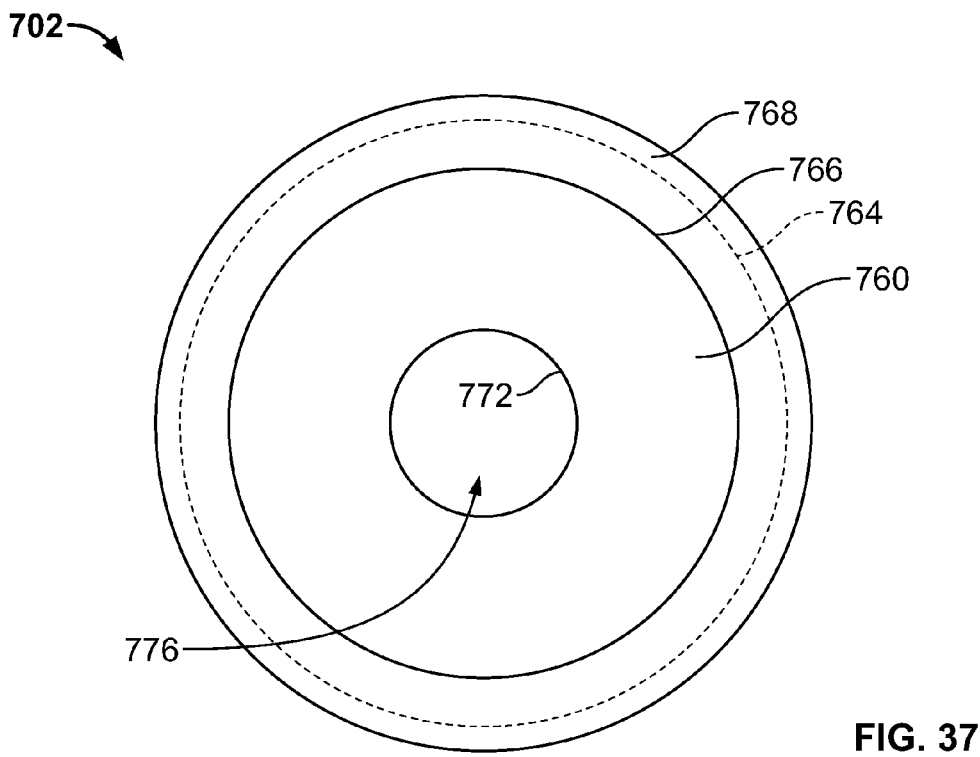

Referring to FIG. 37, the second washer 702 includes opposed top and bottom surfaces 760, 762 that are generally planar and oriented in parallel to one another. Both surfaces 760, 762 include an outer circumferential edge 764, 766 that intersects corresponding circumferential surfaces 768, 770 that are themselves jointed to provide a circumferential boundary for the washer 702. Likewise, both surfaces 760, 762 include an inset, centered circular edge 772, 774 that defines the top and bottom cross-section of a non-threaded through opening 776 that extends between both surfaces. An internal wall 778 is circular in cross section and defines the vertical, lengthwise dimensions of the opening 776. This internal wall 778 is perpendicularly oriented with respect to the lop and bottom surfaces 760, 762. In this manner, the through opening 776 includes a cylindrical shape with a constant horizontal circular cross section along its length that is parallel to the top and bottom surfaces.

At the outer periphery of the second washer 702 are two circumferential surfaces 768, 770. A first of these circumferential surfaces is a sloped surface 768 angled at approximately forty-live degrees with respect to the top surface 760 of the washer 702. It should be noted, however, that the sloped circumferential surface 768 may be angled other than forty-five degrees such as, without limitation, angles ranging between live to seventy degrees are within the scope of the invention. The sloped surface 768 is adapted to act as a bearing surface and interact with the prongs 726 in order to create a spring force pushing the top planar surface 760 of the second washer 702 away from the bottom planar surface 724 of the first washer 703. This sloped surface 768 is circular and defines a portion of the outer periphery of the second washer 702, along with the arcuate circumferential surface 770. The arcuate circumferential surface 770 links the sloped surface 768 and the bottom planar surface 762. This circumferential surface 770 is smooth and mirrors the arcuate profile of the spherical sidewalls 712 of the bone plate 706. In this manner, the arcuate circumferential surface 770 is adapted to be seated against the spherical sidewall 712 of the bone plate 706 so that the vast majority of its surface contacts the spherical sidewall when inserted into the bone plate 706.

As will be discussed in more detail hereafter, the through opening 776 is adapted to receive a shank of a variable angle locking screw (not shown), while the bottom circumferential surface 770 contacts the spherical sidewalls 712 of the bone plate 706. As can be seen in FIG. 40, the washers 702, 703 may be compressed against one another with the prongs 726 of the first washer 703 acting as springs and contacting the sloped bearing surface 768 of the second washer 702. When compressed against one another, the washers 702, 703 may be rotated and axially repositioned within the through hole 704. In sum, the prongs 726 provide a spring force sufficient to inhibit substantial axial and rotation motion of the washers 702, 703 with respect to the plate material 706, However, by compressing the washers against one another, such as upon applying a compressing force against the washers using the variable angle locking screw, the washers 702, 703 may be axially and rotationally repositioned.

Initially, the washers 702, 703 may be compressed against one another as the variable angle locking screw is inserted in order to orient the screw and washers at the desired axial position. In exemplary form, the shaft of the screw is inserted through the openings 776, 736 of the washers 702, 703 until a threaded head of the screw reaches and engages the threads 740 of the first washer 703, at which point compressive force on the screw may be discontinued. Continued downward movement of the screw into the through hole 704 thereafter requires rotation of the screw with respect to the first washer 703 so that the head of the screw is vertically repositioned with respect to the first washer. Eventually, rotation of the screw head results in the bottom of the screw head contacting the top surface 760 of the second washer 702. It should be noted that the diameter of the through hole 776 of the first washer 703 is larger than the diameter of the through hole 736 of the second washer 702, thus inhibiting the screw head from passing into the through hole 736 of the second washer 702. Because the screw head cannot pass beyond the second washer 702, continued rotation of the screw head with respect to the first washer 703 repositions the first washer 703 vertically away from the second washer 702. Specifically, the bottom of the screw head pushes against the top surface of the second washer 702 and forces the arcuate circumferential surface 770 into locking contact with the spherical sidewalks 712 of the plate material 706. Likewise, rotation of the screw head forces the first, washer 703 upward so that the outer circumferential surface 720 contacts the spherical sidewalls 712 of the plate material 706. Eventually, a compression fit is formed by the washers 702, 703 pushing against the spherical sidewalls 712 so that neither the washers nor the screw may be axially repositioned (see FIG. 39). In order to axially reposition the washers and screw, the screw head is rotated in an opposite direction that discontinues the friction fit.

It is also within the scope of the disclosure to switch the prongs 726 and the sloped bearing surface 768. By way of example, the first washer 703 would include the sloped surface 768 as part of its peripheral surface, adjoining the bottom surface 724. Similarly, the top surface 760 of the second washer 702 would include the prongs 726 that extend upward, toward the sloped surface 768 of the first washer 703.

While the spherical sidewall 712 of the bone plate 706 and circumferential surfaces 720, 770 of the washers 703, 702 have been described as being smooth surfaces, it is also within the scope of the disclosure to roughen one or more of these surfaces to increase the exposed surface area. Those skilled in the art are familiar with roughening techniques including, without limitation, powder coating, sand blasting, abrasive polishing, and casting a roughed surface.

Referring to FIG. 40, a fifth exemplary variable angle locking screw assembly 800 includes a deformable washer 802 adapted to be received within a through hole 804 of a bone plate 806. In this exemplary embodiment, the bone plate 806 includes at least one through hole 804 extending from the top surface 808 to the bottom surface 810 of the plate. The through hole 804 is at least partially defined by spherical or bowl-shaped sidewalls 812 operative to change the cross-sectional area of the hole along the vertical length of the hole. Consistent with spherical sidewalls 812, the horizontal cross-sections of the holes are generally circular with varying diameters. Specifically, the diameter of the through hole 804 defined by the spherical sidewalls 812 at the top and bottom surfaces 808, 810 is at a minimum, whereas the maximum diameter is at the vertical midpoint of the hole that generally corresponds to the diameter of a sphere that would fit snuggly within the bounds of the hole. Conversely, for bowl-shaped sidewalls 812, the horizontal cross-sections of the holes are generally circular with diameters that decrease going from the top surface 808 to the bottom surface 810, in exemplary form, the sidewalls 812 are roughened, threaded, or otherwise fabricated so that the walls were not smooth. By way of example, and not limitation, the walls 812 may be fabricated with a plurality of teeth that extend normally toward the axial center of the through hole 804 in order to engage the deformable washer 802.

The deformable washer 802 is fabricated from any biologically compatible material including, without limitation, polyethylene and PEEK (polyether ether ketone). In exemplary form, the deformable washer 802 is ring-shaped and includes an external diameter that is larger than the diameter of the through hole 804. In this fashion, the washer 802 is adapted to deform around a head 816 of a variable angle locking screw 818 when the head is inserted into the through hole 804. The opposed top and bottom surfaces 820, 822 of the washer are generally flat and are vertically spaced apart from one another a distance equal to the thickness of the washer 802. The ring shape of the washer 802 defines a through hole 824 adapted to receive a shaft 826 of the variable angle kicking screw 818. It should be noted that the through hole 824 is sized to inhibit throughput of the screw head 816.

Figure 41:
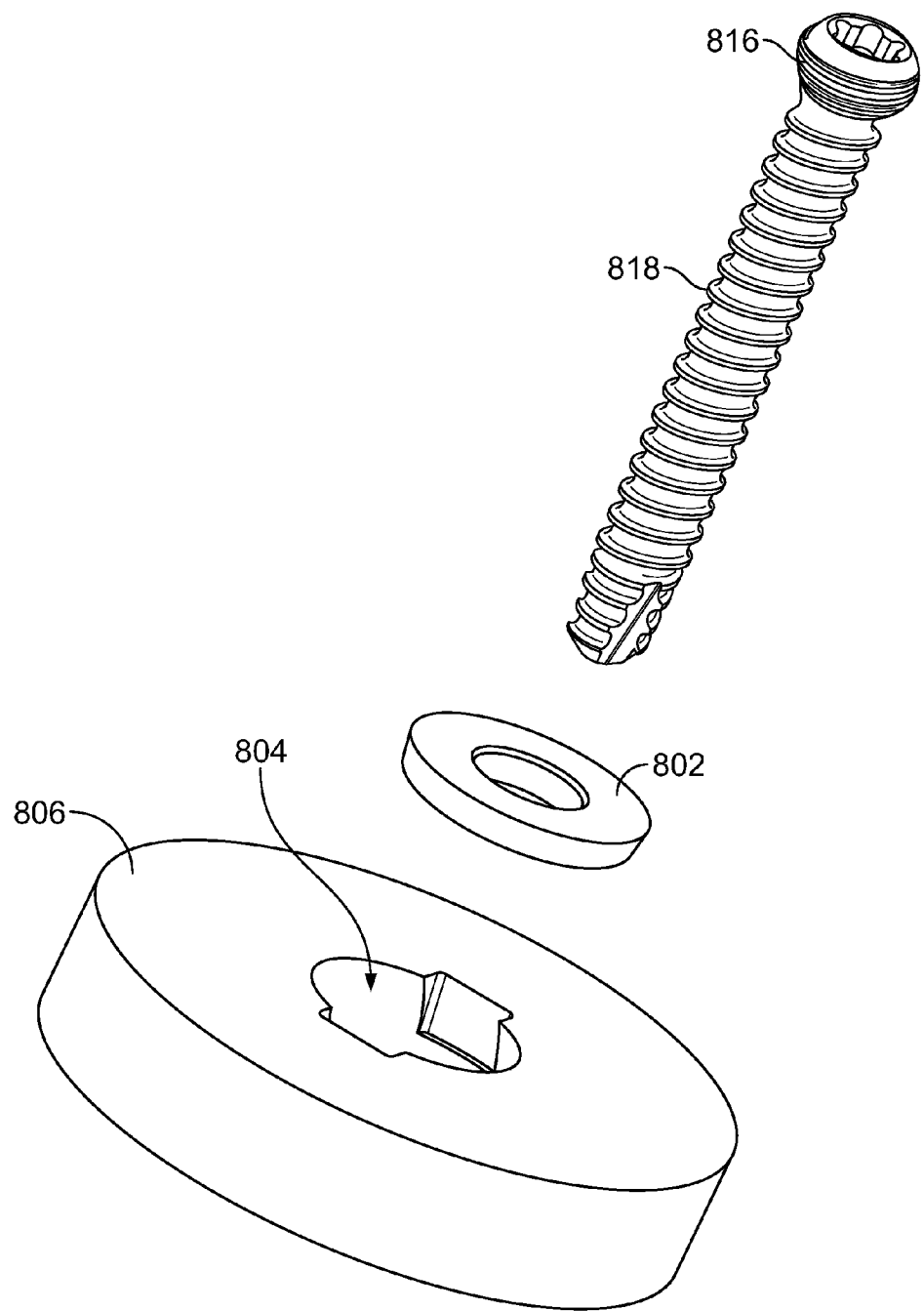
FIG. 41 is an exploded view of a fifth exemplary variable angle, locking screw-assembly.
Figures 42, 43:
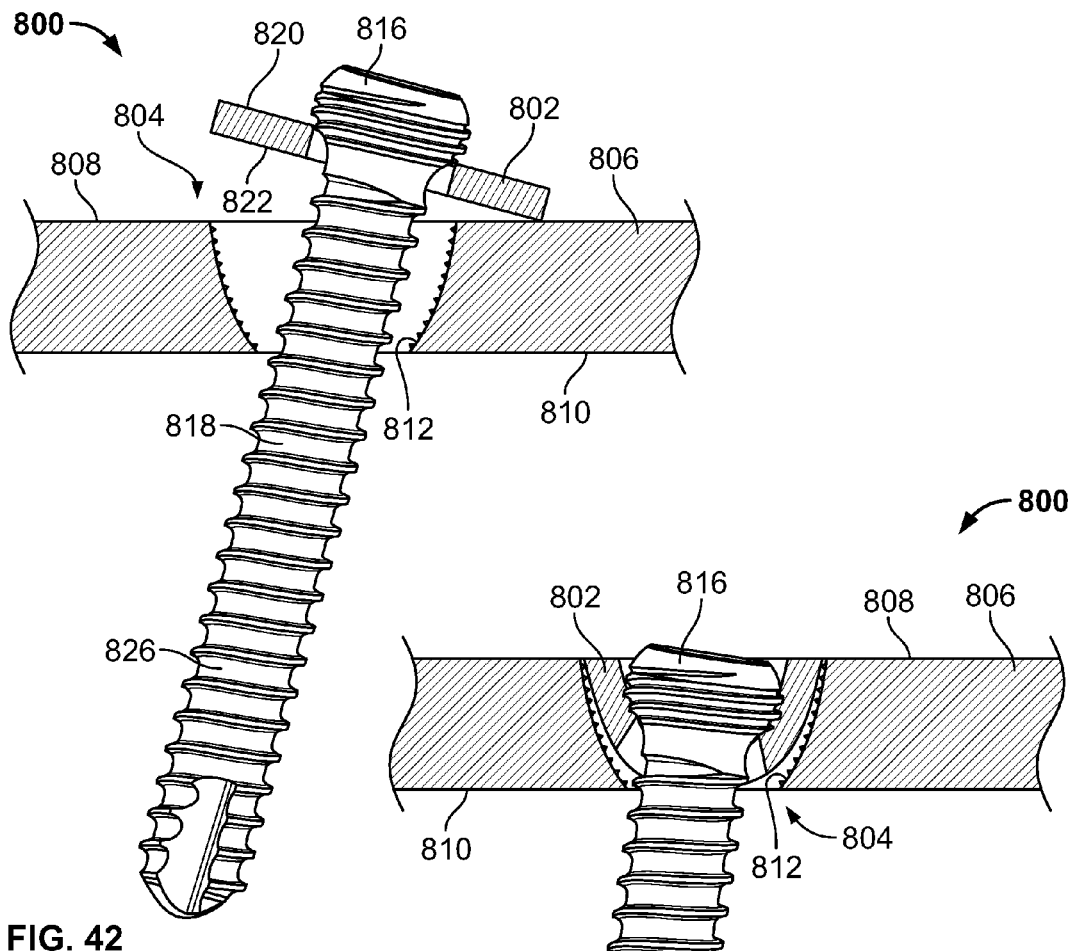
FIG. 42 is a cross-sectional view of the fifth exemplary variable angle locking screw assembly of FIG. 41, prior to the screw being oriented in a locked position.
FIG. 43 is a cross-sectional view of the fifth exemplary variable angle locking screw assembly of FIG. 41, with the screw being oriented in a locked position.

Referring to FIGS. 41 and 42, usage of the exemplary variable angle locking screw assembly 800 requires initially inserting the shaft 826 of the locking screw 818 through the opening 824 of the deformable washer 802 in order to mount the washer to the locking screw. Specifically, the washer 802 is repositioned vertically along the shaft 826 until abutting the underside of the screw head 816. After the washer 802 and locking screw 818 are mounted to one another, the shaft of the 826 of the locking screw is inserted into the through opening 804 of the bone plate 806 and is vertically positioned to engage bone (not shown) on the underside of the bone plate at a particular axial orientation. As the locking screw 818 is rotated with respect to the bone plate 806 and the bone underneath the plate material, the head 816 of the locking screw and deformable washer 802 are advanced into the through opening 804 of the bone plate 806. Rotation of the screw 818 is operative to pull the head 816 and washer 802 further into the through opening 804. Initially, upon reaching the opening 804, the cross-section of the washer 802 cannot pass into the opening without being deformed. The force of the screw 818 is operative to pull the washer 802 into the opening 804, which also results in the washer deforming around the screw head 816. Otherwise, the screw head 816 and the washer 802 could not be advanced into the through opening 804. As the screw head 816 is drawn deeper and deeper into the through opening 804, the washer increases its conformity and occupies an area in between the plate material 806 and screw head in a compression fit (see FIG. 42). In this manner, the force on the screw 818 creates a friction fit between the screw, the washer 802, and the plate material 806 in order to lock the axial orientation of the screw with respect to the plate material. In order to axially reposition the washer 802 and the screw 818, the screw head 816 is rotated in an opposite direction that discontinues the friction fit.

Figure 44:
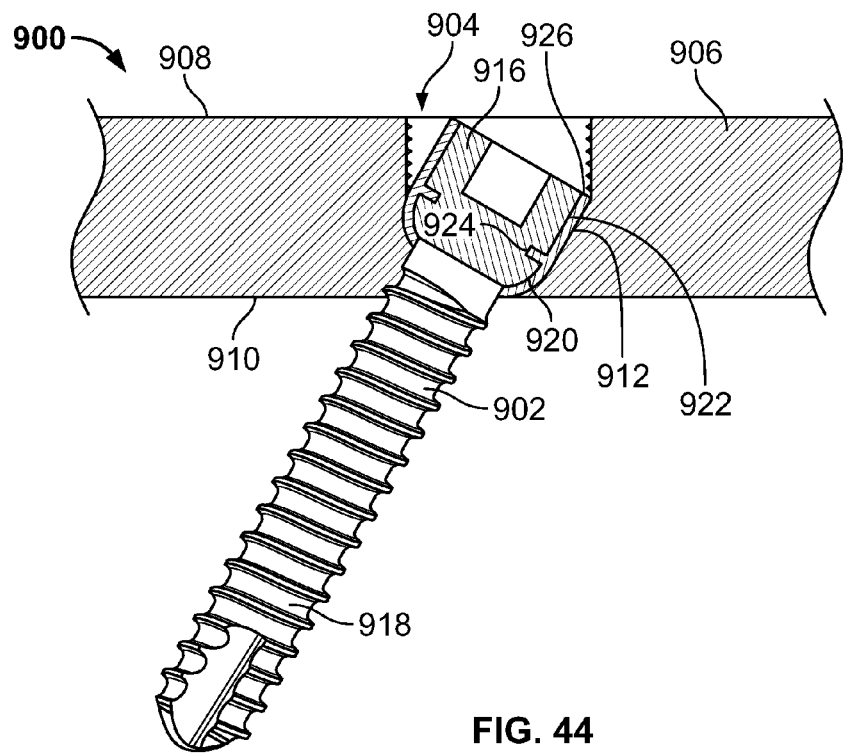
FIG. 44 is a cross-sectional view of a six exemplary variable angle locking screw assembly.
Figure 45:
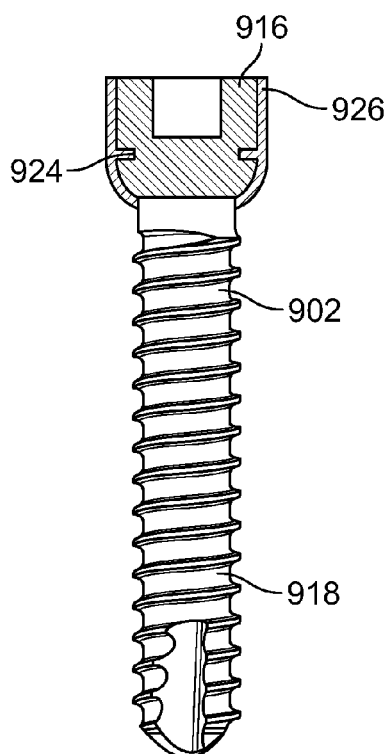
FIG. 45 is a cross-sectional view of an exemplary variable angle locking screw comprising part of the variable angle locking screw assembly of FIG. 44.
Figure 46:
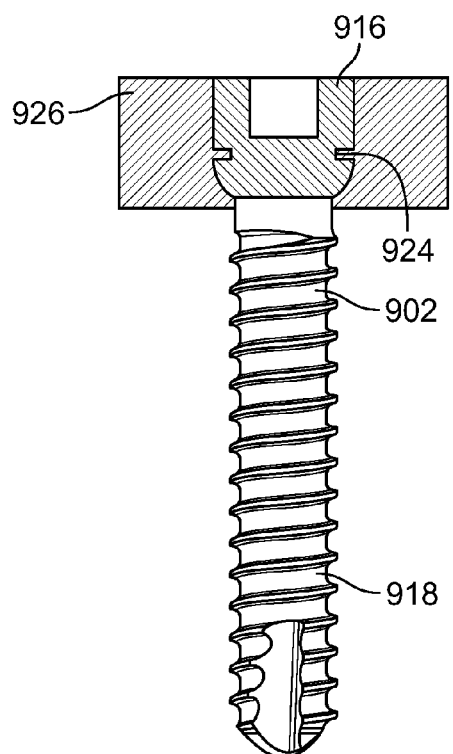
FIG. 46 is a cross-sectional view of an exemplary variable angle locking screw comprising pan of the variable angle locking screw assembly of FIG. 44, prior to machining of the over-molded cap.

Referencing FIGS. 43-45, a sixth exemplary variable angle locking screw assembly 900 includes variable angle locking screw 902 adapted to be received within a through hole 904 of a bone plate 906 in order to lock in the axial orientation of the screw. In this exemplary embodiment, the bone plate 906 includes at least one through hole 904 extending from the top surface 908 to the bottom surface 910 of the plate. The through hole 904 is at least partially defined by spherical or bowl-shaped sidewalls 912 operative to change the cross-sectional area of the hole along the vertical length of the hole. Consistent with spherical sidewalls 912, the horizontal cross-sections of the holes are generally circular with varying diameters. Specifically, the diameter of the through hole 904 defined by the spherical sidewalls 912 at the top and bottom surfaces 908, 910 is at a minimum, whereas the maximum diameter is at the vertical midpoint of the hole that generally corresponds to the diameter of a sphere that would fit snuggly within the bounds of the hole. Conversely, for bowl-shaped sidewalls 912, the horizontal cross-sections of the holes are generally circular with diameters that decrease going from the lop surface 908 to the bottom surface 910. In exemplary form, the sidewalls 912 are roughened, threaded, or otherwise fabricated so that the walls were not smooth. By way of example, and not limitation, the walls 912 may be fabricated with a plurality of teeth that extend toward the center of the through hole 904 in order to engage the locking screw 902.

The locking screw 902 includes an enlarged head 916 coupled to an elongated, threaded shaft 918. The enlarged head 916 includes a bowl-shaped bottom 920 that transitions into a cylindrical top 922. Interposing the bowl-shaped bottom 920 and the cylindrical top 922 is a circumferential channel 924 that is adapted to provide a foothold for a deformable material molded onto the head 916 to create a cap 926. In this exemplary embodiment, the cap 926 is fabricated from any biologically compatible, deformation material including, without limitation, polyethylene and PEEK (polyether ether ketone). The cap 926 may be over-molded into an end-use shape (see FIG. 44) or require machining to shape the cap in its end-use shape (see FIG. 45).

Referring to FIG. 43, usage of the exemplary variable angle locking screw assembly 900 requires initially inserting the shaft 918 of the locking screw 902 through the opening 904 of the bone plate 906. This positioning includes positioning the screw 902 to engage bone (not shown) on the underside of the bone plate at a particular axial orientation. As the locking screw 902 is rotated with respect to the bone plate 906 and with respect to the bone underneath the plate material, the head 916 of the locking screw is advanced into the through opening 904 of the bone plate 906. Rotation of the screw 902 is thereafter operative to pull the head 916 further into the through opening 904. As the head 916 is drawn further into the through opening 904, the cap 926 interacts with the sidewalls 912 of the bone plate 906. Specifically, the teeth extending from the sidewalks 912 dig into the cap 926 in order to inhibit axial repositioning of the locking screw 902. In other words, the locking screw 902 wedges the cap 926 in between itself and the bone plate sidewalls 912 to create a friction fit that lock the axial orientation of the screw. In order to axially reposition the screw 902, the screw is rotated in an opposite direction that discontinues the friction fit.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A locking screw assembly comprising:
    a plate material having a through hole at least partially defined by a semispherical wall;
    a first washer at least partially defining a first opening and being insertable into the through hole, the first washer including a widthwise dimension substantially greater than a thickness and comprising circumferentially spaced threaded wall segments, each pair of adjacent threaded wall segments being interposed by a circumferential discontinuity;
    a second washer at least partially defining a second opening and being insertable into the through hole, the second washer includes a widthwise dimension substantially greater than a thickness;
    a screw insertable into the through hole and including a threaded head that is configured to threadably mate with the threaded wall segments of the first washer, the screw further including a longitudinal threaded shaft extending from the threaded head; and a driver configured to interact each circumferential discontinuity of the first washer to prevent rotation of the first washer while the screw is inserted into the through hole;

wherein the first opening and second opening are sized to allow throughput of the longitudinal threaded shaft; and wherein the semispherical wall is sized to retain the first washer and the second washer within the through hole.

2. The locking screw assembly of claim 1, wherein at least one of the first washer and the second washer includes a rounded circumferential surface interposing a top surface and a bottom surface.

3. The locking screw assembly of claim 1, wherein a wall at least partially defining the first opening of the first washer is threaded.

4. The locking screw assembly of claim 3, wherein a wall defining the second opening of the second washer is not threaded.

5. The locking screw assembly of claim 1, wherein:
the longitudinal threaded shaft of the screw includes threads having a first pitch and a first thread depth;
the threaded head of the screw includes threads having a second pitch and a second thread depth;
the first pitch is greater than the second pitch; and
the first thread depth is greater than the second thread depth.

6. The locking screw assembly of claim 1, wherein the second opening of the second washer is at least partially defined by a rounded over surface extending between a horizontal top surface and a wall of the second opening.

7. The locking screw assembly of claim 1, wherein the second opening of the second washer is sized to inhibit throughput of the threaded head of the screw.

* * * * *

UNITED STATES PATENT AND TRADEMARK OFFICE
CERTIFICATE OF CORRECTION

PATENT NO. : 8,728,129 B2
APPLICATION NO. : 12/986879
DATED : May 20, 2014
INVENTOR(S) : Fritzinger et al.

It is certified that error appears in the above-identified patent and that said Letters Patent is hereby corrected as shown below:

In the Claims

Column 31, Claim 1, line 4, please insert the term --with-- before the term "each"

Signed and Sealed this
Eighth Day of July, 2014

Michelle K. Lee
*Deputy Director of the United States Patent and Trademark Office*